United States Patent [19]

Mohlenbrock et al.

[11] Patent Number: 5,018,067

[45] Date of Patent: May 21, 1991

[54] APPARATUS AND METHOD FOR IMPROVED ESTIMATION OF HEALTH RESOURCE CONSUMPTION THROUGH USE OF DIAGNOSTIC AND/OR PROCEDURE GROUPING AND SEVERITY OF ILLNESS INDICATORS

[75] Inventors: William C. Mohlenbrock, Del Mar; Peter J. Farley, Orinda; Lawrence J. Frye, Atherton; Donald E. Trummell, Jr., Daly City; Alan G. Bostrom, San Francisco, all of Calif.

[73] Assignee: Iameter Incorporated, San Mateo, Calif.

[21] Appl. No.: 79,654

[22] Filed: Jul. 29, 1987

Related U.S. Application Data

[63] Continuation-in-part of Ser. No. 2,133, Jan. 12, 1987.

[51] Int. Cl.$^5$ .................. G06F 15/21; G06F 15/42
[52] U.S. Cl. .................. 364/413.02; 364/413.01
[58] Field of Search .................. 364/414–415, 364/413.02, 413.01

[56] References Cited

U.S. PATENT DOCUMENTS 4,667,292  5/1987  Mohlenbrock .................. 364/406
4,731,725  3/1984  Suto .................. 364/413

FOREIGN PATENT DOCUMENTS 0028834  3/1977  Japan .................. 364/415
0822200  4/1981  U.S.S.R. .................. 364/413

OTHER PUBLICATIONS

Kreitzer et al., *QRB/Quality Review Bulletin*, May 1982, pp. 21–34.
Horn et al., Inquiry, vol. XX, Winter 1983, pp. 314–321.
Mendenhall, *Modern Health Care*, Nov. 15, 1984, pp. 86 and 88.
Young, *Health Care Financing Review*, Nov. 1984, pp. 23–31.
Panniers et al., *QRB*, Feb. 1985, pp. 47–52.
*Medicine and Health Perspectives*, McGraw-Hill, Mar. 11, 1985.
Brewster et al., *Inquiry*, vol. XXII, Winter 1985, pp. 377–387.
Grant Application dated Nov. 4, 1985 to Health Care Financing Administration (HCFA).
Horn et al., Medical Care., Mar. 1986, vol. 24, No. 3, pp. 225–235.
Young, *American Medical Record Association Journal*, Mar. 1986, pp. 29–33.
Horn et al., *American Journal of Public Health*, May, 1986, pp. 532–535.
"AIM" Brochure of Iameter Incorporated, early Sep. 1986.
Horn, *Healthcare Financial Management*, Oct. 1986, pp. 21–32.
Graves et al., Report of Commission on Professional and Hospital Activities, Ann Arbor, Mich.
"Clinical/Financial Information Systems," Report of Commission on Professional and Hospital Activities, Ann Arbor, Mich.

*Primary Examiner*—Charles E. Atkinson
*Assistant Examiner*—Gail O. Hayes

[57] ABSTRACT

The likely consumption of health provider resources that are necessary to treat a particular medical patient are estimated within the framework of the existing Federal mandated system that uses Diagnostic Related Groups (DRG's) for setting the amount of payment that a hospital or other health provider will receive from the United States Government for that patient under the Medicare reimbursement system. The amount of payment is made from a calculation using the DRG system, regardless of the actual cost to the health provider. The Federal system results in a wide variation of health care costs occurring within each DRG, resulting from varying degrees of overall sickness among patients that are similarly classified. The present invention works within the DRG system and all of the sub-groups of DRG's including groups of diagnosis codes and individual diagnosis codes. Hidden information is extracted from the same input data that is used by the DRG system, in order to classify each patient into sub-categories of resource consumption, or other outcome variable, within a designated DRG or DRG sub-group. The invention is implemented by a general purpose computer system.

27 Claims, 6 Drawing Sheets

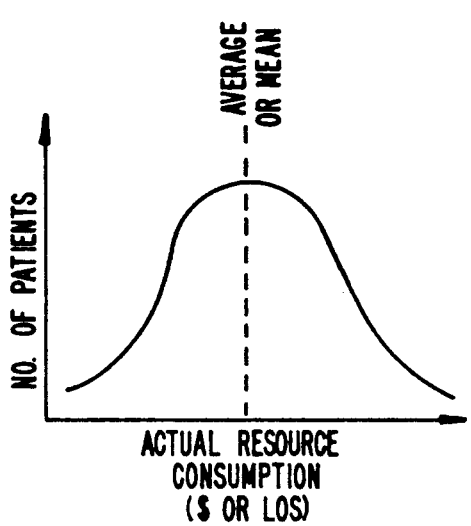
FIG._1.-
DISTRIBUTION OF RESOURCE CONSUMPTION FOR A PATIENT POPULATION WITHIN A SINGLE DRG
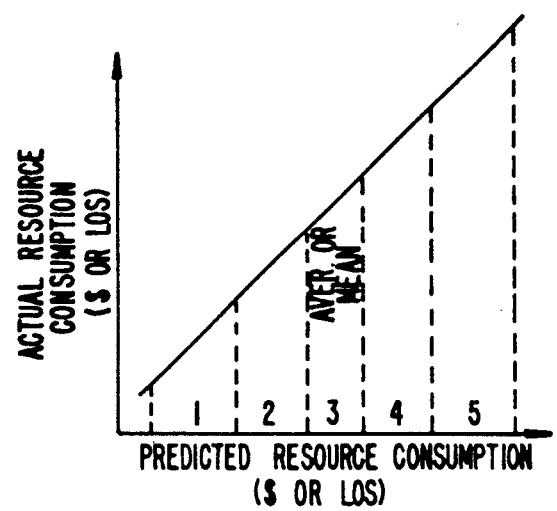
FIG._2.-
EXAMPLE CLASSIFICATION OF PREDICTED RESOURCE CONSUMPTION INTO 5 ACUITY INDEX CATEGORIES FOR ONE DRG
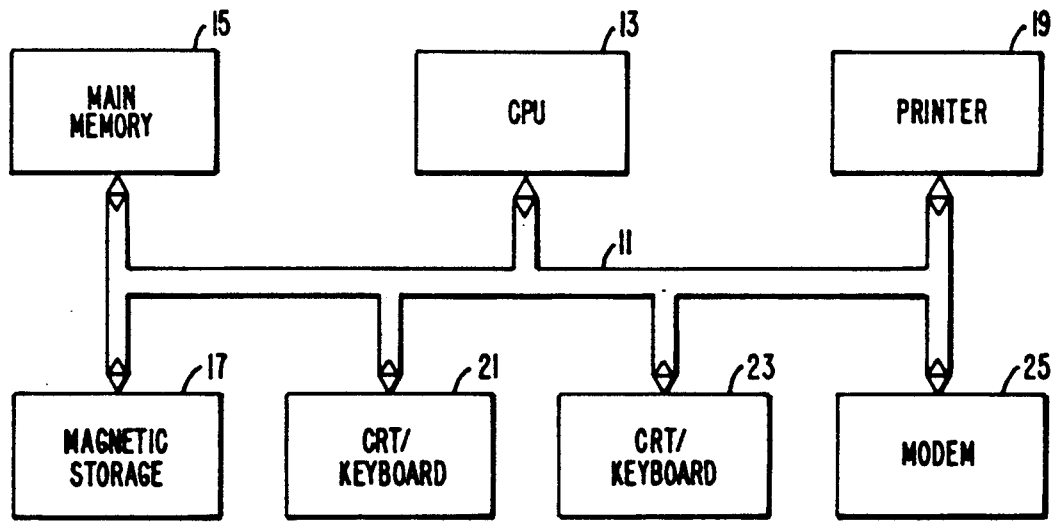
FIG._3.

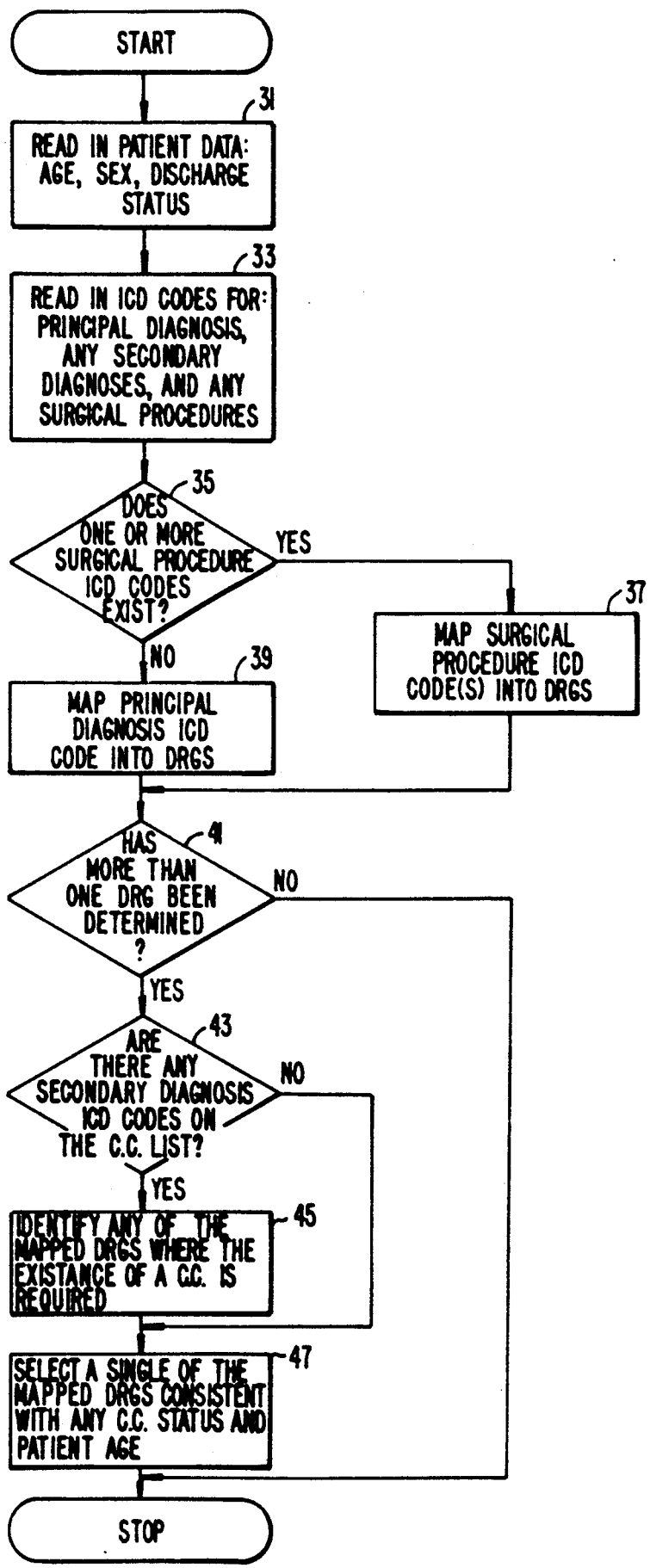
FIG._4.
PRIOR ART

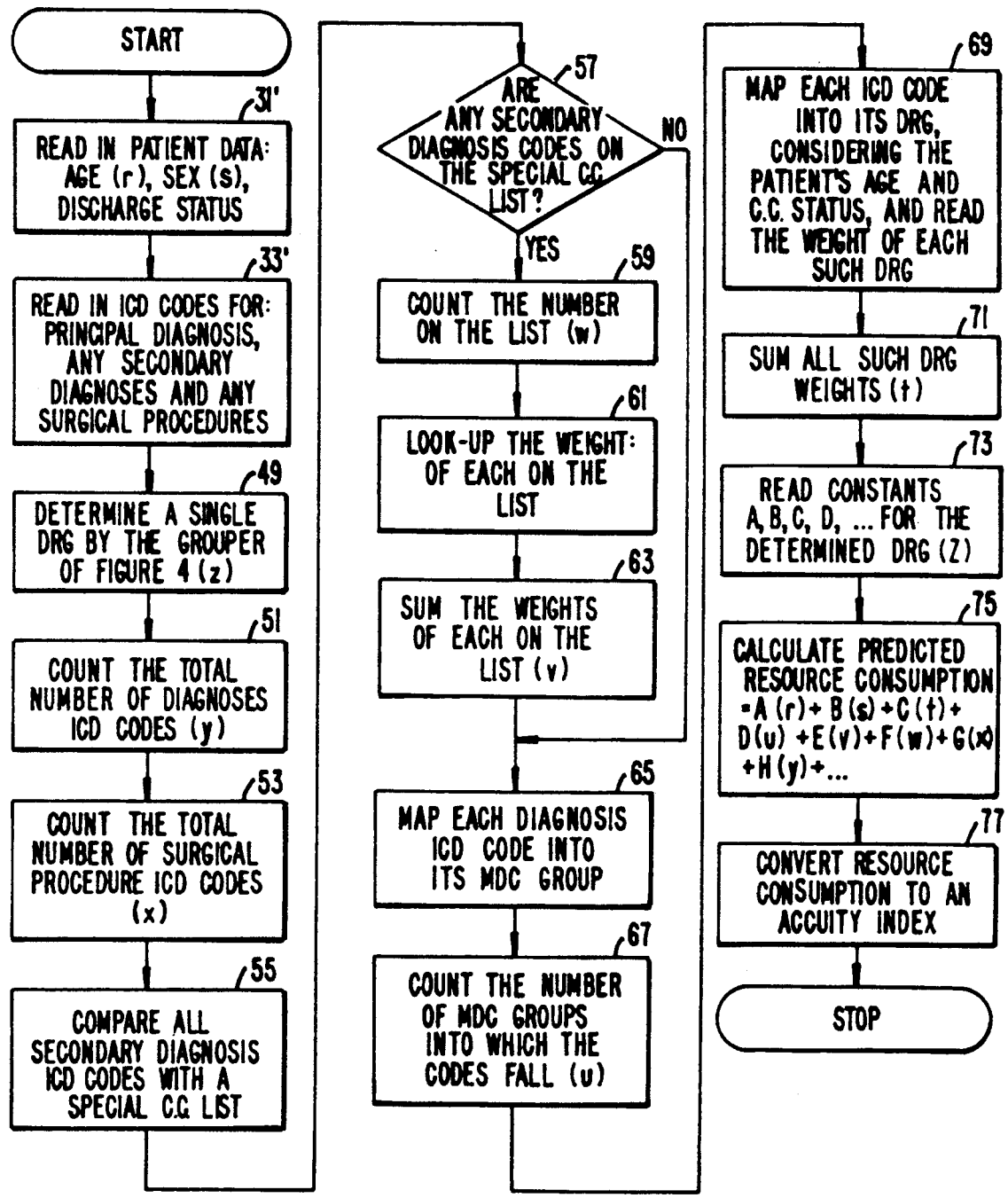
FIG._5.

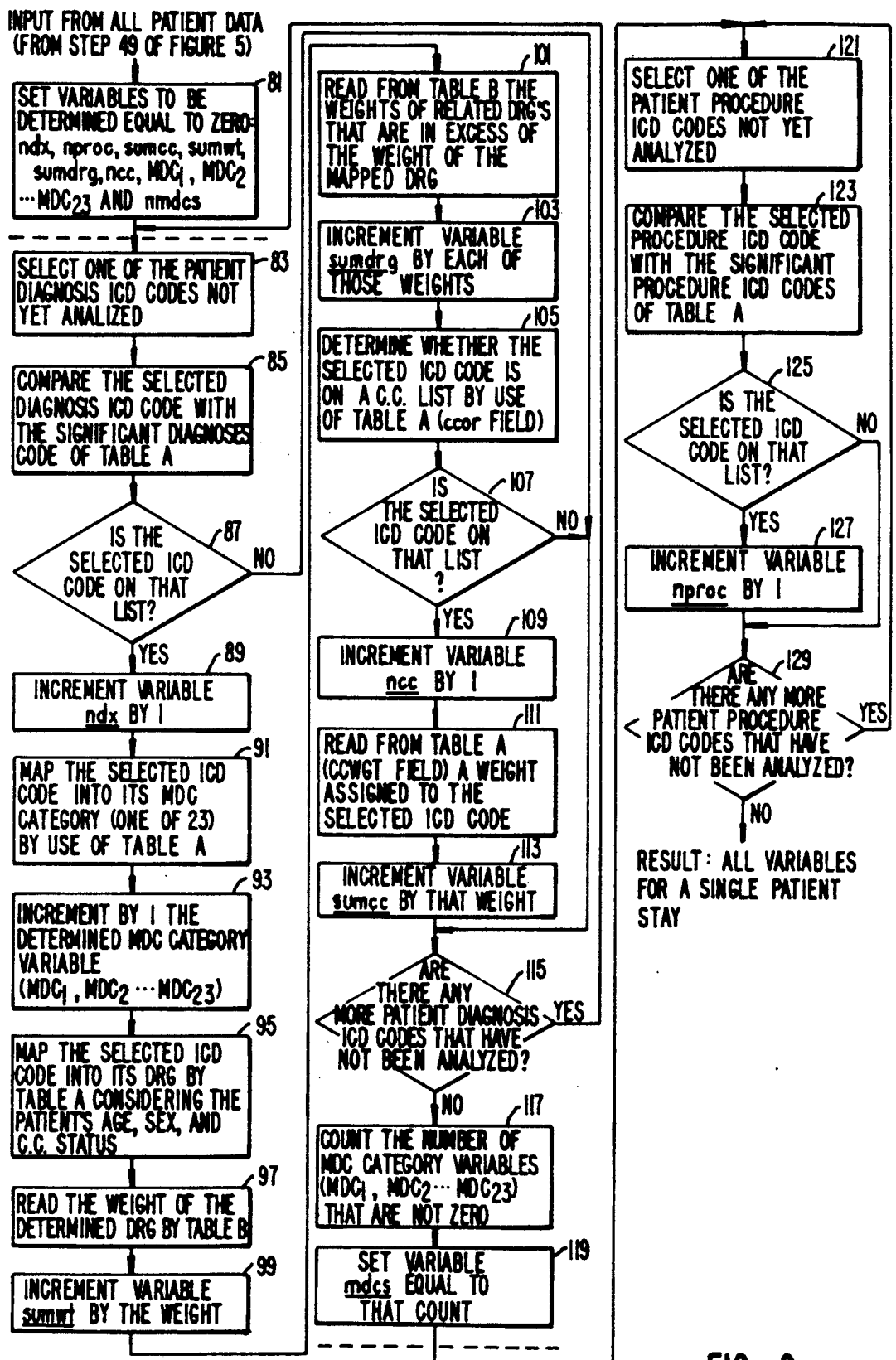
FIG._6.

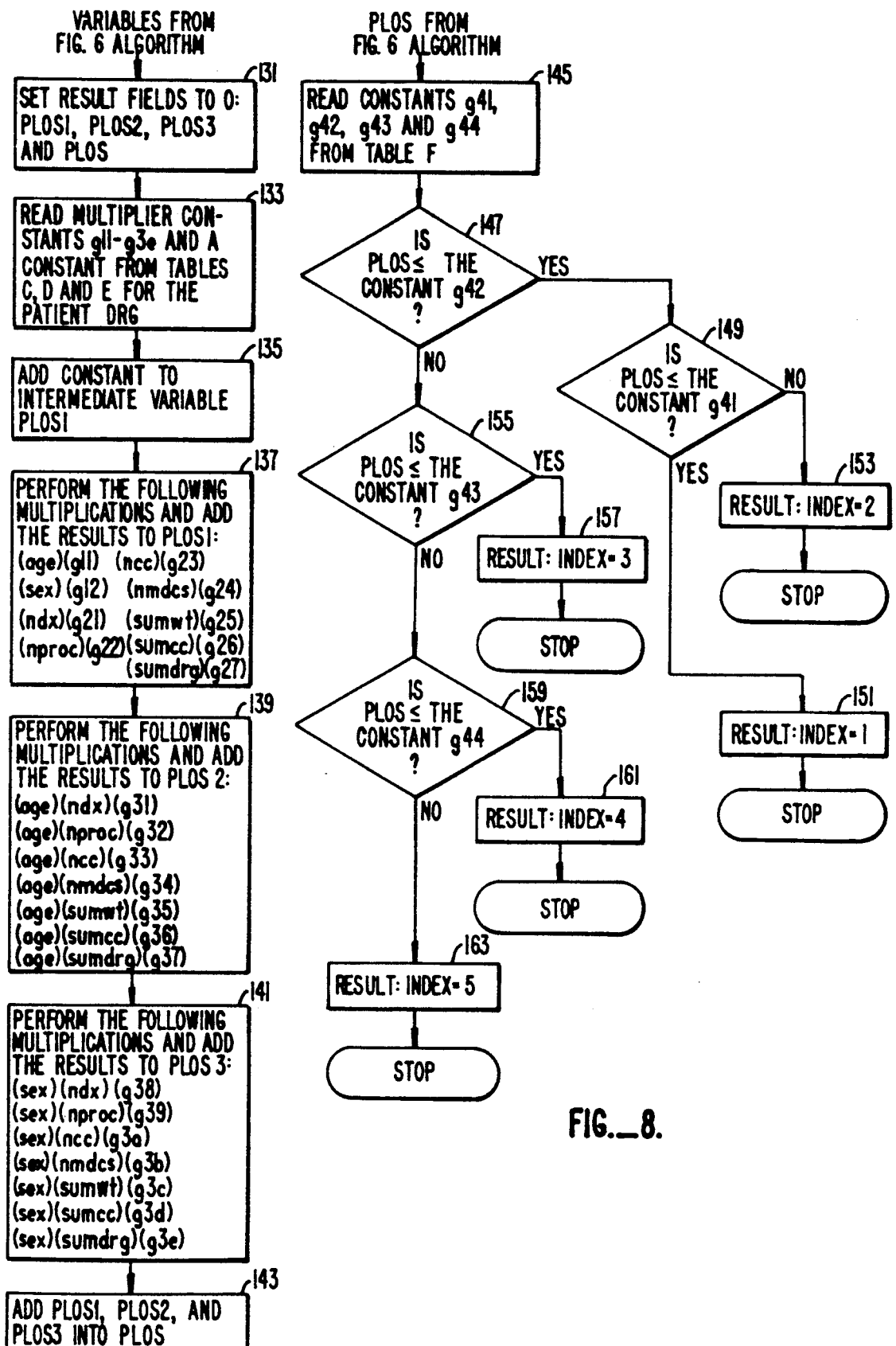

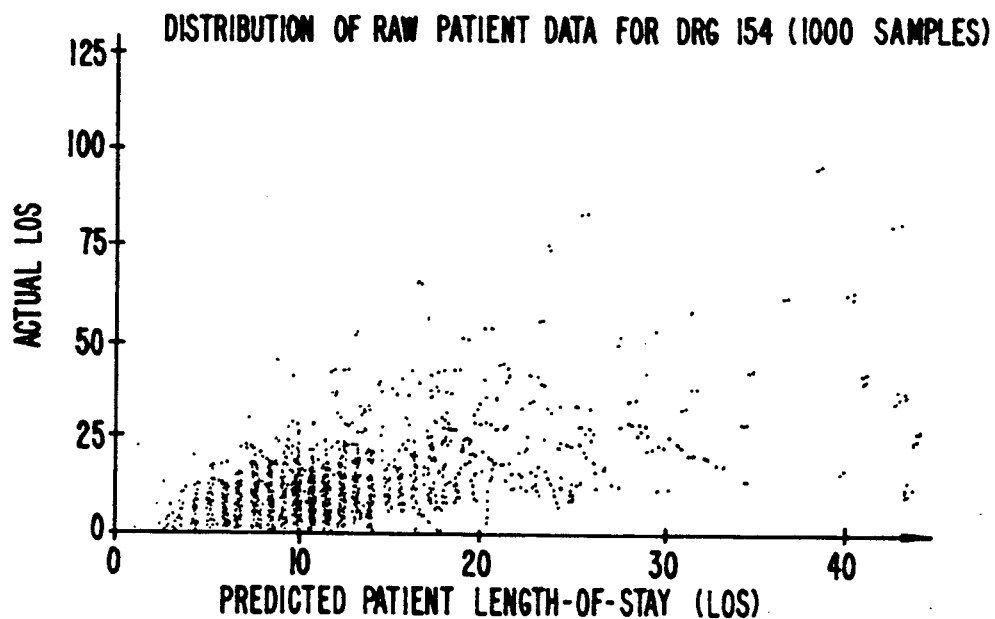
FIG._9.
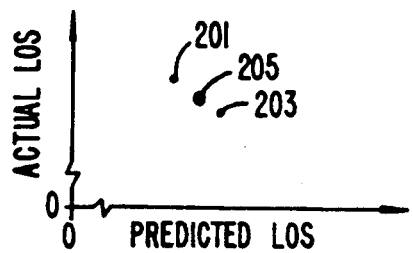
FIG._10.
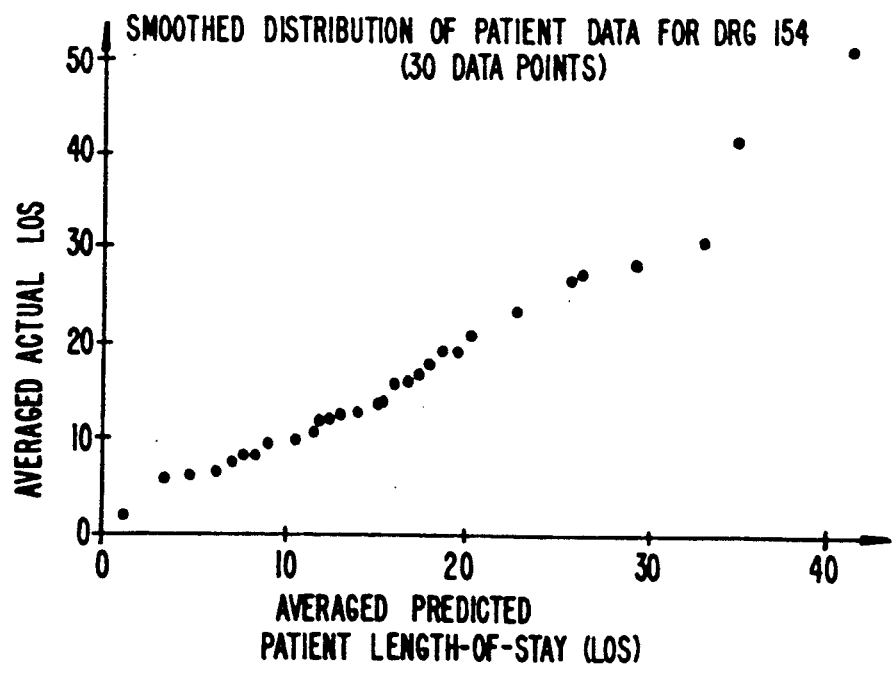
FIG._11.

APPARATUS AND METHOD FOR IMPROVED ESTIMATION OF HEALTH RESOURCE CONSUMPTION THROUGH USE OF DIAGNOSTIC AND/OR PROCEDURE GROUPING AND SEVERITY OF ILLNESS INDICATORS

CROSS-REFERENCE TO A RELATED APPLICATION

This is a continuation-in-part of pending application Ser. No. 07/002,133, filed Jan. 12, 1987.

BACKGROUND OF THE INVENTION

This invention relates generally to the identification of quality and cost efficient medical providers, and specifically to computer software techniques and systems for estimating what the cost to treat a patient should be, based upon the condition of the patient and to the extent that any treatments or procedures impact the patient's health status.

Due to the geometric escalation of medical care costs, there is increased pressure on public policy makers to establish cost containment programs. For this reason state and Federal governments are beginning to adopt various case specific or case-mix reimbursement systems. The Social Security Amendments of 1983, (Public Law 98-21), introduced a diagnosis specific prospective payment system that has been incorporated into the Medicare reimbursement policies. Under this system, the amount of payment for a patient hospital stay is determined by a one of hundreds of government defined Diagnostic Related Groups ("DRGs") into which the patient stay is categorized based upon diagnoses and procedures performed. Hospitals are reimbursed according to a fixed schedule without regard to actual costs to the hospital in rendering medical services to the patient. It is expected that this same reimbursement policy will in time be extended to establish the level of reimbursement to other health care providers and/or from other government entities and insurers.

The DRGs represent a statistical, clinical classification effort to group together those diagnoses and procedures which are clinically related and have similar resource consumption. A DRG that is appropriate for a given hospital stay is selected, under the reimbursement system, by a particular set of patient attributes which include a principal illness diagnosis, specific secondary diagnoses, procedures performed, age, sex and discharge status (i.e., how the patient left the hospital, whether the patient was transferred, died, etc.). The principal diagnosis is that which caused the patient to be hospitalized, even though the patient may have even more serious problems, as would be indicated by secondary diagnoses. If a surgical procedure is performed, the DRG is determined primarily by that procedure. If no procedure is performed, the DRG is determined primarily by the principal diagnosis. The treatment of a patient during a single hospital stay is classified in only one DRG.

As shown in the few examples of DRGs given in Table I attached hereto, a fixed reimbursement factor (relative weight) is assigned to each DRG by the government. This determines the amount the hospital will be reimbursed for treatment of a patient that falls within the DRG, regardless of the hospital's cost or what the charges would have been for a non-Medicare patient. The more complex diagnoses or procedures that typically consume more resources should result in a higher paying DRG. (See the different relative weights in the example DRG's of Table I.) In addition to the reimbursement factor, each DRG has an average length of stay (LOS) in days assigned as another measure of the consumption of resources that is expected to treat a patient whose attributes cause that particular DRG to be selected.

There are currently 473 DRGs which cover all patients treated under inpatient conditions. These are set forth in the regulations of the Health Care Financing Administration. The example DRGs of Table I attached hereto are taken from those regulations. Since adoption of the system, regulations have been issued annually that make some changes in classification details to take into account experience under the system.

Under the current version of this reimbursement system, the hospital does not directly determine the appropriate DRG category for services rendered a Medicare patient. Rather, the hospital submits an appropriate Federal form (currently form UB-82) after discharge of the patient, which includes codes from a standard coding system to identify the primary and secondary diagnoses made, and any procedures performed, and gives patient information that is relevant to determining the appropriate DRG category, such as age and sex. As an alternate to using such a form, the coded information can be submitted on magnetic media, such as tape, in computer readable form. From this information, an intermediary reimbursing agent, or the Health Care Finance Administration itself, determines the proper DRG, and thus the amount of reimbursement.

The commonly used notation "ICD-9-CM" means the International Classification of Diseases—9th Revision, Clinical Modification, and refers to a coding system based on and compatible with the original international version of the ICD-9 coding system provided by the World Health Organization. The ICD-9-CM coding system is used in North America, and it is a classification of diseases, injuries, impairments, symptoms, medical procedures and causes of death. These codes are listed in detail in a publication of the Commission on Professional and Hospital Activities, Ann Arbor, Michigan, entitled "ICD-9-CM", Jan. 1, 1979. It is likely that the classification system will be revised and a 10th revision forthcoming within a few years. The techniques being described herein are not limited to a particular version of the ICD diagnosis and procedure classification system but rather will use whatever system is current at the time. As a shorthand reference to that system, the term "ICD" will be used hereinafter, unless a specific version is being discussed as an example.

The ICD coding system was designed for the classification of morbidity and mortality information for statistical purposes and for the indexing of hospital records by disease and operations for data storage and retrieval. The ICD codes are initially divided into Disease and Procedure sections. These sections are further divided into subsections which encompass anywhere from 1-999 three digit disease or 1-99 two digit procedure code categories. Within the three digit code categories there can be an additional 1 or 2 decimal digits to divide the codes into subcategories which further define the disease manifestations and/or diagnostic procedures. There are approximately 15,000 ICD codes. Only a portion of these are relevant for determining Medicare payments. The DRG Medicare payment system first involves the coding of diagnostic and procedural information into ICD code numbers by hospital medical records clerks before a patient can be assigned a DRG.

Each DRG is determined in part by an ICD code for the principal diagnosis, and ICD codes for each procedure that may have been performed. There are also ICD codes for identifying complications occurring during treatment, and the existence of any co-morbidities (i.e., secondary diagnoses of conditions other than the principal disease existing at the time of admission). These, as well as the patient's age, sex, and discharge status, determine a particular DRG for the patient.

It is possible that a large number of sets of ICD numbers or codes can lead to the same DRG. Table II attached hereto lists the ICD-9-CM codes that currently fall within each of a few of the DRGs that are used as examples in Table I. The existence of any one operative surgical procedure ICD-9-CM code listed under DRG 261, for example, will cause that DRG to be selected. The remaining DRG examples of Table II (numbers 31, 32 and 33) each have the same list of ICD-9-CM codes that will cause a DRG to be selected. A single one of these related DRGs is then selected based upon the age of the patient and whether there exists any complication or co-morbidity (referred to together as a "C.C." in the DRG definitions) as evidenced by an appropriate secondary diagnosis ICD-9-CM code.

A patient's age is a part of the definition of many of the DRG categories, as shown by the examples of Tables I and II. Pediatric patients (age 17 or less) and elderly patients (age 70 years or more) often fall into separate DRG categories that otherwise have the same textual definition. Where this occurs, the hospital is paid more for treatment of the older patient by assigning a higher paying DRG.

Also, the presence of a complication or comorbidity (C.C.) with a patient is a part of the definition of many DRGs. A patient with a complication or comorbidity is considered to be a sicker person for certain illnesses than one without a C.C. and the hospital is reimbursed more for those illnesses by classifying such a patient in a higher paying DRG. However, not all medically recognized complications or comorbidities are recognized by the DRG reimbursement system to have any effect on the payment to be made. The DRG Medicare system currently specifies about 3000 of the approximately 15,000 ICD-9-CM codes as effective to establish a C.C. and thus provide higher reimbursement. That is, if any one of these approximately 3000 ICD-9-CM codes appear as a secondary diagnosis on the patient discharge information, a C.C. is deemed to exist. Thus, if the patient is otherwise classified into a family of DRGs where the existence of a C.C. makes a difference, the higher paying DRG is selected from the family. For example, with regard to the family of DRGs 31, 32 and 33 of Tables I and II which have the same lists of principal diagnoses ICD-9-CM codes, both the patients age and the existence or non-existence of a C.C. determines which of the three DRG categories is selected for reimbursement purposes. It should be noted that the relative weight and mean length of stay (LOS) definitions of those three DRGs vary widely.

The actual reimbursement that a hospital receives for each patient involves the multiplication of the relative weight of the DRG (see Table I) with other factors set by the Federal government. These other factors are determined by statistical variables (e.g. cost data of that particular hospital for a period, the type of patients a hospital treats in relation to the hospital's resources expended for those patients, and the wage and cost of living index).

Computer software is available for calculating the appropriate DRG from the input codes that are provided by the hospital. A DRG Grouper System converts the ICD codes of a patient's stay, along with the other DRG related factors (age, sex, discharge status), are mapped into the corresponding DRG category. This is public information that is available at cost. One company manufacturing an enhanced DRG Grouper is the DRG Support Group, Ltd., a subsidiary of Health Systems International, Inc.

Because such a large proportion of hospital patients fall under the Medicare system (40% or more of the patients of some hospitals), the DRG system is extensively used. It is natural, therefore, that the system would also be used for health care management and evaluation purposes. However, it is widely recognized that the grouping of patients resulting from use of the DRG system does not have as high a degree of homogeneity as is statistically desirable. That is, the resource consumption of a population of patients, who all are classified into a single DRG, varies widely. The statistical deviation from the single mean length of stay (LOS) for most of the DRGs is large, apparently because the overall level of sickness of the patients so grouped varies widely. The sicker patients require more hospital resources to be devoted to them but the DRG Medicare system considers this only to a limited extent by selecting a DRG primarily from only a single principal diagnosis made or surgical procedure performed.

As a result, there have been many suggestions for refining the DRG system, or to go to a different system, in order to result in a more homogeneous grouping of patients. The reasons for doing so include the need to have data for monitoring hospital and physician performance, as well as improving the reimbursement system itself. The suggested approaches include many different ways to measure how sick a patient really is.

The primary variable in any patient population which must be taken into account before either mortality and morbidity rates or resource consumption can be addressed is that of the patient diagnosis. If a physician is asked to predict the mortality rate of a group of patients, the first question he or she will ask is "What is the diagnosis?". The expected mortality rates between a fractured wrist and cerebrovascular accident (stroke) are very different. The DRGs are a very adequate way of subdividing the patients on the basis of their diagnoses.

The second and crucial variable is that of the severity of the patient's illness within each of the various diagnoses. An example is that some myocardial infarctions (heart attacks) are fatal, and some go completely unnoticed by the patient, representing a wide variation in severity. The DRGs do not have the ability to adequately determine the acuity (severity) of the patient's illness within the diagnostic categories.

It is a primary object of this invention to provide a computer based technique and system for estimating the severity of patients' illnesses from hospital discharge data and other medical information, and for estimating the resources likely to be consumed in the course of providing medical service to patients, all with improved accuracy and convenience.

SUMMARY OF THE INVENTION

This and additional objects are accomplished by the present invention wherein, briefly and generally, in a specific form, a computer system is provided for calculating the severity of patients' illnesses and thereby providing an estimate of resource consumption from the same information that is used as a basis for determining the DRG. This has a significant advantage in that the necessary data is readily available in a form to be directly used in making the estimate, often stored on computer magnetic media so that it can be fed directly into a computer making the estimate, perhaps even the same computer that is determining the appropriate DRG. In a preferred embodiment of the invention, no further information about the patient and his or her condition is required. Hidden clinical information is extracted by the resource estimating system from the ICD codes and other available input data in order to make an estimate. This input data is combined by the computer according to a formula (a linear equation, in a preferred embodiment) that includes a set of constants that exist in a static data base for each DRG included in the system. Variables of the formula can include, for example, the number of different ICD codes (particularly any secondary diagnosis codes) specified by the health provider to describe the condition of patient during a particular hospitalization, a sum of the Government weights for each of the DRGs into which the ICD codes (particularly the diagnosis codes) are mapped, and a sum of relative weights assigned to certain ICD codes that, when specified as secondary diagnosis, indicate a sicker patient than is communicated by the principle diagnosis code alone.

A set of such constants is determined for a given DRG by a process of statistically analyzing a set of actual patient data for that DRG by use of the same formula. The variables of the formula, including outcome, specific diagnoses codes, etc., are in this case known for each actual patient. In effect, a separate formula is established for each such patient record. A statistical computer program then determines a set of constants for use in the formula for the given DRG which minimizes variances between the actual known outcomes and those estimated by use of the formula.

In a preferred form, the estimated outcome is expressed in one of several categories (such as categories 1 through 5) for the DRG that has been determined for the patient, and represents a much more homogeneous grouping of patients than is provided by the DRG categories themselves, because it is based upon various levels of illness severity within each diagnosis. Because physician and hospital providers can then be compared on the basis of a homogeneous patient population, it becomes possible to identify those providers whose practice patterns are of the highest quality and most cost efficient.

There are two primary applications for such a system other than to objectively calculate the amount of payment to the health provider. One is a retrospective: the cost performance of a physician, hospital, or expense of an insurance plan, for example, can be compared to the estimate for one, a few, or a large number of patients. That is, a set of actual costs incurred are compared with the estimates. This is quite a useful tool since the estimates are made by formulas whose constants have been calculated from a large amount of actual patient data.

The other primary application is concurrent: the expected cost of treating a patient may be determined upon admission of the patient to the hospital from the initial diagnosis and expected procedures. Any problem cases identified by such estimates can then be managed more intensively than others. Further, any changes occurring during the hospital stay, primarily the addition or change of any of the secondary diagnosis data, can evidence missed or erroneous initial diagnoses or complications caused by disease progression or improper treatment, thus providing a tool for monitoring hospital and/or physician performance.

Additional objectives, features and advantages of the various aspects of the present invention will become apparent from the following description of its preferred embodiment, which description should be read in conjunction with the accompanying drawings.

BRIEF DESCRIPTION OF THE DRAWINGS

FIG. 1 is a curve that illustrates the distribution of costs in treating patients who all are classified into the same DRG;

FIG. 2 is a curve that illustrates the further classification that results from the techniques of the present invention;

FIG. 3 shows a block diagram of a typical computer system that may be utilized to practice the present invention;

FIG. 4 is a flow diagram that shows the general operation of public domain software that determines the appropriate DRG for the purpose of reimbursing a health provider for services to a particular patient;

FIG. 5 is a flow diagram of a computer program which operates w the computer system of FIG. 3 in carrying out various aspects of the present invention, according to a first example;

FIGS. 6-8 provide a flow diagram of a computer program which operates with the computer system of FIG. 3 in carrying out various aspects of the present invention, according to a second example; and FIGS. 9-11 illustrate a portion of the process for calculating the value of constants used in the computer program examples of FIGS. 5-8, according to another aspect of the present invention.

DESCRIPTION OF THE PREFERRED EMBODIMENTS

General Discussion of the Invention

The non-severity adjusted, and therefore non-homogeneous grouping of patients, that results in many Diagnostic Related Groups (DRGs) of the DRG Medicare reimbursement system is illustrated in FIG. 1. The number of patients classified in a single DRG is plotted against their actual resource consumption incurred in treatment, in terms of charges or mean length of stay (LOS) of the patient in the hospital. The fact that the distribution deviates significantly from the single mean LOS used in the DRG system as a basis for payments shows the need to modify the system when a high degree of certainty in estimates of resources consumed is required.

Therefore, according to the present invention, a sub-category of resource consumption is calculated in addition to determining a DRG by the usual method. This sub-category, referred to herein as the "acuity index", is calculated from the same information used to determine the DRG, as described in detail later in this description.

Hidden clinical information of the overall level of sickness of a patient, not now used by the DRG system, is extracted from input data common to the DRG system. By using the same input data, a simplicity in implementation results. By expressing the result of an acuity index within the DRG system, there is conformity with a system familiar to health care professionals.

FIG. 2 shows an idealized plot of actual resource consumption for a given patient population in a single DRG versus resource consumption that is estimated (predicted) by the techniques of the present invention. Rather than give as a result the estimated LOS or other quantitative indication of resource consumption, the estimated resources are expressed as falling within one of five acuity indices for that particular DRG. Acuity index number 1 includes the patients requiring the lowest amount of resources within the given DRG. Acuity index number 5 includes the patients with the highest estimated resource consumption. Acuity index number 3 generally includes the government calculated mean LOS within it. Of course, the exact number of subgroups selected for use in any system depends upon its specific application.

Before describing the method of determining the acuity index for any given patient, a computer system used to calculate both the DRG and acuity index for a patient is outlined. Referring to FIG. 3, the main components of a computer system that is suitable for implementing the various aspects of the present invention is shown. Connected to a common computer bus 11, are several operational units that form the computer system. These are a central processing unit (CPU) 13, a main R.A.M. memory 15, a disc drive 17, a printer 19, and an entry keyboard and CRT terminal 21. A second such terminal 23, and perhaps even additional terminals, can be provided as desired. A modem 25 is optionally provided to add a communication capability.

A principal magnetic disc data file that is part of the system of FIG. 1 is that containing information of all the DRGs. It is accessible by the disc drive 17. The DRG file is a static computer database having one record for each DRG number. Table I shows seven fields of information for each of the example DRGs given. This information is that published as part of the Federal regulations. The first stored item of information is the DRG number, some unique number between 1 and 473. The next item of information, shown in the second column of Table I, is the Major Diagnostic Category (MDC) in which the individual DRG falls. The 473 specific DRGs are grouped by the Federal regulations into 23 MDCs of related DRGs. Each MDC is defined to include the DRG's directed to matters of a different body system than the others The third column of Table I identifies the sex of the patient for which the individual DRGs are appropriate. A "B" means the DRG is appropriate for both sexes, a "F" for female only, and a "M" for male only. This field is compared with the sex of the patient to check for an erroneous DRG determination.

The fourth item of information for each DRG maintained in the static DRG database is shown in the third column of Table I, namely the title or textual description of the DRG. What is shown in Table I are all of the items published in the Federal Register. It will be noticed that the textual descriptions are very brief, so it may be desirable to expand that description into medically relevant terminology for the purpose of the DRG database herein.

The fifth data field, shown in the fifth column of Table I, is a relative weight for each DRG. As discussed above, this determines the amount of compensation that is given a hospital for treating a patient whose diagnosis and/or procedures cause a particular DRG to be designated.

The same is true for each of the last two items of Table I. The column "Mean LOS" is a calculated average length of stay for a patient within the DRG. The "Outlier Cutoffs" column carries information of a maximum length of stay in days that should be allowed. These last two items of information are desirably printed whenever information as to its DRG is printed in order to provide hospital staff with these guides, but they are not otherwise used in the computer system to be described.

It will be noted from the titles in Table I that some of the DRGs include an operative patient age range for their operation, and whether a C.C. (complication or co-morbidity) is required for that DRG to apply. The existence of a C.C. follows from a secondary diagnosis ICD code that is one of about 3000 put on a special list by the current Federal system as indicating a sicker patient that justifies higher compensation. Note from the titles of the DRGs in Table I that DRGs 34 and 35 have the same titles except for the reference to the patient's age and the existence of a C.C. A patient with a principal diagnosis that indicates "other disorders of the nervous system" will be classified into DRG 35 unless the patient is either over 69 years of age or has a C.C. If the patient is older than 69 or has a C.C., then DRG 34 is appropriate. Note that the relative weight and mean LOS of DRG 34 is greater than those of DRG 35. DRGs 34 and 35 are referred to as a "doublet" since they result from a common principal diagnosis; the appropriate DRG is then determined from the age and C.C. data.

DRGs 96, 97 and 98 are a "triplet" since they all deal with bronchitis and asthma, the particular DRG depending upon age and/or C.C. status. DRG 261 is given as an example of a single DRG that is applicable to a particular diagnosis and/or procedure. The patients age or C.C. status is not important for classification when such a DRG is the appropriate one.

The DRG table database is a static one and the same for all hospitals. For the computer system to operate, certain information of the patient is also required, primarily his or her age and sex. This information can be entered directly when the computer system is being operated, or, preferably, is maintained in a dynamic current patient file database along with other information of the patient, such as name, date of admission, attending physician's name, billing and medical record numbers, and the like.

Table II attached hereto is a list of the ICD-9-CM codes specified by the Federal DRG Medicare regulations for four example DRGs from Table I. If any ICD code on one of those lists exists as a principal diagnosis or surgical procedure performed, this will result in the particular DRG under which the ICD code falls to be designated for reimbursement purposes, under the Federal system. DRGs 31, 32 and 33 form a triplet, having identical ICD codes mapped into them but differing by the age and C.C. requirements.

Public Domain Grouper Operation

Referring to FIG. 4, the overall operation of the public domain grouper software will be explained, in order that its relationship to the acuity index calculating techniques of the present invention will become apparent. The determination of an appropriate DRG under the Federal regulations for a given patient's stay in the hospital begins with inputting relevant information. A step 31 of the flow chart of FIG. 4 calls for reading in various patient data, most important of which is age, sex and discharge status. Remaining input information necessary to make a DRG determination is indicated at step 33 of FIG. 4, namely a listing of ICD codes that are provided by the hospital or other type of health provider. These codes can either be extracted from the Federal form UB-82 used by hospitals to apply to Medicare for payment, or the codes, as well as the patient data, may already be in a computer readable form on magnetic tape or some other storage media.

There will always be at least one ICD code provided by the hospital, that being to identify the principal diagnosis of the patient's condition. This is defined to be that condition which caused the patient to come to the hospital in the first place. In addition, there may be some ICD codes that indicate secondary diagnosis of a patient's condition observed during hospitalization or treatment. Finally, if a surgical procedure was performed on the patient, there will be one or more ICD codes to identify the procedure or procedures that were performed.

If a surgical procedure was performed, that will be controlling in determining the DRG for medical payment purposes. A step 35 of FIG. 4 inquires whether there are any surgical ICD codes for a particular patient. If so, a step 37 is performed wherein initial determination of potential DRG categories is made based upon the surgical procedures performed. If not, the principal diagnosis ICD code is used in a step 39 to determine potential DRG categories. There is always only a single principal diagnosis ICD code, so step 39 is rather straightforward. However, there can be multiple surgical procedure ICD codes, if more than one procedure is performed on the patient, so the step 37 is somewhat complicated. A single one of the procedure ICD codes is selected by use of a Federally mandated hierarchy which gives greater weight to some procedure ICD codes than others.

At the step 41, the one or more potential DRG categories determined by either of the steps 37 or 39 is then observed to determine whether there are indeed multiple DRGs selected as possibilities. It is most common that only one DRG category is selected, but there are a number of doublets and triplets, described above, where an operative ICD code maps into two or three DRG categories. As described previously, the single appropriate DRG category is selected from a doublet or triplet on the basis of the patient's age and the existence or non-existence of a complication or co-morbidity (C.C.).

Therefore, if the operative ICD code has been mapped into doublet or triplet DRGs, then it is determined in a step 43 whether there are any secondary diagnosis ICD codes for the patient which were inputted in step 33, and, if so, whether any of these secondary diagnosis codes are on a "C.C. list". The "C.C. list" includes about 3000 of the 15,000 ICD codes which are designated by the Federal regulations as indicating a condition that could consume extra resources of a health provider in treating the principal condition of the patient. If the particular stay of the patient for which the DRG is being determined according to the algorithm of FIG. 4 includes such a secondary diagnosis ICD code, then a next step 45 determines which of the doublet or triplet DRGs includes the existence of a C.C. in its definition. The definitions of DRGs have previously been described with respect to Table I attached to this application. Once that has been done, then the existence of the C.C. and the age of the patient is used in a step 47 to select only one DRG from the doublet or triplet that were identified in either of the steps 37 or 39.

Of course, if only one DRG is identified in either of the steps 37 or 39, the process skips from step 41 down to the end. That is, in the cases where only a single DRG is selected from mapping the appropriate ICD code into the DRG definitions, the patient's age or existence of secondary conditions is ignored for the purposes of determining an amount of payment to a hospital for treating that patient. Those factors are not part of the definition of such a DRG.

First Example of Estimating an Outcome

FIG. 5 outlines the major steps of the technique of the present invention for arriving at an acuity index that indicates the relative level of sickness of the patient within a large population of patients for whom the same DRG has been determined, according to one example. The method purposely relies upon the same information from which the DRG is determined since that information is readily available from the patient's hospital chart, and perhaps already in computer data form. Referring to FIG. 5, the initial data input steps 31' and 33' deal with the same information as the steps 31 and 33 of the DRG grouper system of FIG. 4. For purposes of a calculation described later, certain of patient dependent quantities are given mathematical notations. The variables of age and sex are denoted in this discussion, as "r" and as "s", respectively. The patient's sex is quantified in standard hospital coding by making "s" equal to 1 for a male, and 2 for a female patient.

A next step 49 is to calculate the DRG for the particular patient hospital stay being examined, and the resulting DRG is given the variable notation "z". Usually, the selected DRG will simply be another item of input information to the algorithm indicated in FIG. 5. Alternatively, a DRG grouper algorithm of FIG. 4 can be incorporated into the system of FIG. 5. In either case, it is the determination of the DRG that is important since the acuity index to be calculated is stated within the single resulting DRG category.

The system of FIG. 5 extracts a great deal more information from the input data than is used to determine the DRG under the existing reimbursement system. The goal is to extract the data that tells us how sick the patient really is, and then to determine the amount of resources that are likely to be necessary to treat the patient, within a range of resources typically expended on patients within the determined DRG.

Referring again to FIG. 5, a specific example of the system that extracts hidden information from the input information to the DRG system is described. A step 51 counts the total number of diagnoses ICD codes for the patient. This includes the principal diagnosis and any secondary diagnoses. The total number of such codes is designated by the variable "y".

Similarly, a step 53 counts the number of surgical procedure ICD codes in order to determine the variable indicated by "x". The DRG grouper does not use the total number of ICD codes any where, but it has been found that this is one indication as to how sick the patient is.

The next series of operations illustrated in FIG. 5 uses secondary diagnoses ICD codes as two additional variables in the acuity index calculation algorithm. A step 55 compares each of the secondary diagnosis ICD codes for the patient to a "C.C. list". The Federally mandated DRG payment system already has a "C.C. list" list of approximately 3000 ICD codes that make some difference in the amount of payment if they appear as secondary diagnoses for a patient. This list of about 3000 ICD codes is categorized into levels of severity. In the specific example being described, three levels of severity are used. The C.C. list of relevant diagnosis ICD codes, and their weight, are determined by physician review and forms a part of the static data base used in the acuity index calculation method being described.

Step 57 determines whether any secondary diagnoses ICD codes are on such a C.C. list. If not, then the next several steps are skipped, but if one or more codes are on that list, a next step 59 is to count the number. This number is indicated as a variable "w" and adds additional information as to how sick the patient really is. A next step 61 is too look up the weight for any such secondary diagnosis ICD code that has been assigned. The weights in this system are either 1, 2 or 3, the higher number indicating a condition existing as a secondary diagnosis that is likely to make a patient sicker than those coded with the lower numbers. A next step 63 adds the weights for all such ICD codes to determine a single quantity "v". The amount of this variable has also been found to be related to the overall sickness of the patient.

The next two steps 65 and 67 of FIG. 5 obtains information from the organization of the DRG system itself. As previously mentioned, the DRGs are organized into 23 major diagnostic categories (MDCs). Each MDC groups together the DRGs relating to a single system of the human body. Step 65 of FIG. 5 identifies the various MDC groups in which the patient's diagnoses ICD codes fall. By the definition and organization of the DRG system itself, an ICD code is specified to fall within only one MDC group of DRGs. A principal diagnosis ICD code will fall into one MDC. If there are secondary diagnoses ICD codes, individual ones may fall in other MDCs. This is determined in step 65, and the total number of MDCs into which the diagnoses ICD codes fall is counted in a step 67. This count is the value of another variable "u" and has been found to be related to the level of sickness of the patient. If more body systems are involved, the patient is likely to be sicker.

The next steps 69 and 71 effectively perform a portion of the DRG grouper algorithm illustrated in FIG. 4. Rather than first selecting a single ICD code that is used to determine the DRG for payment purposes, as is done in the DRG Medicare reimbursement system illustrated in FIG. 4, each ICD code for the patient is mapped into its corresponding DRG, taking into account the DRG definition for the patient's age and C.C. status. That is, a single DRG is determined for each of the diagnoses and procedure ICD codes of the patient. The relative weights of the determined DRGs (see the fifth column of Table I) are added together in a step 71 to determine the value of another variable "t". These steps use information available from the DRG system itself that is not otherwise presently used, as a factor in measuring the level of patient sickness.

As indicated in the steps 73 and 75, each of the determined variables "r" through "t" are used in a mathematical formula to calculate the estimated resource consumption for that patient. The resource consumption is calculated by use of a linear equation including sums of terms including these variables multiplied by a constant. Each of constants "A" through "H" are multiplied by one of the variables described above to from a single term of a linear equation indicated in step 75 of FIG. 5. A sum of those terms gives the desired estimated resource consumption for the patient.

The constants of the formula of step 75 are different for every DRG and are part of a static data base used in making the calculation of FIG. 5. Those constants are preferably determined by statistically analyzing a great deal of actual patient data. That is, the input data, calculated DRG and actual resource consumption, usually expressed in terms of length of stay (LOS) of the patient in the hospital, are used along with the formula of step 75, to calculate these constants for that DRG. A standard available statistical analysis computer program is preferably used to do this. An example of such a use is given in more detail hereinafter in the section entitled "Determining Algorithm Constants".

In addition to the terms of the formula of step 75 including a constant times a single variable, it has also been found to be statistically relevant for certain variables to be multiplied together, and then with another constant, as additional terms of the equation of step 75. Various other additions or modifications are possible within the framework of the common goal to extract more information as to the sickness of the patient from the ICD codes regularly kept for the patient for purposes of Medicare payments.

At the end of step 75 of FIG. 5, the amount of resource consumption for this patient has been estimated. This information is useful as an end in itself, but it is preferable to normalize that information within each DRG by simply indicating as an end result of the program one of the acuity index numbers 1-5, as indicated in FIG. 2. A step 77 of FIG. 5 makes the conversion from the estimated resource consumption to one of the five acuity indices.

Information used in the step 77 includes the break points of predicted resource consumption between the acuity indices. Such break points are provided for each DRG as part of the static data base used by the algorithm of FIG. 5. These break points are initially calculated as the result of analyzing a great deal of actual patient data. An example of such a calculation is given in more detail hereinafter in the section entitled "Determining Algorithm Constants" and by the computer programs included herewith as Appendices A and B.

Second Example Of Estimating an Outcome

The algorithm illustrated with respect to FIG. 5 may be considered to have four general functional parts. The first part, including steps 31', 33' and 49, relate to obtaining information of the patient from hospital records or other source. A second part, comprising steps 51-71, computes the value of variables for that patient from such data. A third part, steps 73 and 75, uses those variables to calculate a predicted outcome of the patient's treatment, namely an estimated length of stay (LOS) in the hospital. A final part of that example algorithm, shown as step 77, classifies that length of stay into one of a few acuity indices for the DRG in which the patient's stay is classified for reimbursement purposes.

A second example of such an algorithm is described with respect to the computer software flow charts of FIGS. 6, 7 and 8. In the course of executing the algorithm, static data is also acquired from memory resident tables, an example of the organization of which is given in sample Tables A-F hereto. This algorithm is a refinement of that discussed with respect to FIG. 5, and is given in somewhat more detail, specifically illustrating a particular computer implementation of it.

The algorithm of FIGS. 6-8 has the same four basic functional parts as does that described with respect to FIG. 5. The first functional part of the software is the same as that described with respect to FIG. 5 so is not again shown in any of the flow diagrams 6-8. That part corresponds to steps 31', 33' and 49 of FIG. 5. The patient specific information, already available in hospital records, is read into the computer as data which is used as a source of the calculations shown in FIG. 6-8.

The second major part of the algorithm is illustrated in FIG. 6. This part has as a goal the calculation of seven variables from this patient data. The nomenclature given these seven variables in this description is as follows:

1. ndx—number of input diagnosis codes;
2. nproc—the number of procedure ICD codes;
3. ncc—a sum of all of the diagnosis ICD codes that have a "cc" status (that is, which relate to a complication or co-morbidity);
4. sumwt—the sum of the weights assigned by the Federal Government to the DRG's into which the diagnosis ICD codes map;
5. sumdrg—a sum of the Government assigned weights for some of the DRG's that are related to those in which the diagnosis ICD codes are mapped;
6. sumcc—a sum of relative weights assigned to those diagnostic ICD codes which have a cc status; and
7. nmdcs—the total number of MDC's, or body systems, into which the diagnostic ICD "map".

In addition, there are 23 additional intermediate variables that are used for the calculation, namely $MDC_1$, $MDC_2 \ldots MDC_{23}$. These intermediate variables are used in calculating the variable nmdcs, described below in detail.

As a first step 81 in the processing illustrated in FIG. 6, all of these ultimate variables and intermediate variables are initialized with the value of 0. The following steps 83-119 calculate a value of six of the seven variables from all of the diagnosis ICD codes, both the principal diagnosis and any and all secondary diagnoses, as well as from the DRG into which the patient's stay has been classified, and the patient's age and sex. The processing is shown to take place on one diagnostic ICD code at a time, until all of the codes have been processed.

In a step 83, one of these diagnosis ICD codes is selected and, in step 85, the selected code number is compared with a list of ICD codes in Table A to see if it is on the list. Only those codes considered significant to the determination of severity of illness are included on that list. The example of Table A shows, for a few actual ICD codes, actual data related to them.

If the current selected ICD code is not on that list, then the processing immediately proceeds to step 115. In that case, the selected ICD code is not used in the determination of any of the six variables for which the diagnosis ICD codes are utilized.

If the step 87 finds that the selected diagnosis ICD code is on the list of Table A, then it proceeds to increment the variable ndx by 1. This variable has initially been set at 0 and is incremented by 1 for each diagnosis ICD code that is the object of processing; that is, those that are found in Table A. When the processing for this patient has been completed, therefore, the value of the variable ndx will be a total count of the number of diagnosis codes in that patient's record that are considered significant enough to reside on the list of Table A.

The next step 91 is to determine the MDC category of the Federal Regulations into which the selected ICD code maps. This is accomplished by Table A. For example, ICD code 0040 maps into MDC category 6, as indicated in column 6 of Table A. (The "D" preceding the ICD code number of column 1 of Table A identifies it as the diagnosis ICD code. Similarly, a "P" precedes the procedure ICD codes.)

A next step 91 increments by 1 a record corresponding to the MDC category into which the ICD code is mapped. In the case of ICD code 0040, it is the variable $MDC_6$ that is incremented by 1. After all of the diagnosis ICD codes for a given patient have been analyzed, steps 117 and 119 utilize that information in order to determine the variable mdcs.

Steps 95, 97 and 99 of FIG. 6 show the calculation of the sumwt variable. A first step 95 is to map the selected ICD code into its DRG, and this is 10 accomplished by the use of Table A. Columns 2-5 of Table A provide the possible DRG categories into which the ICD code can be mapped. The operative column in this table depends upon the patient's age and sex. For example, if the patient is male under the age of 70, column 2 provides the DRG into which the selected ICD code is mapped. Conversely, the patient is a female that is age 70 or older, the appropriate DRG is found in column 5. The appropriate one of the columns 2-5 is read in step 95.

In step 97 of FIG. 6, that DRG is applied to Table B, and the weight assigned to that DRG by the Federal Government is given in column 2 of that table. The actual weights for a few DRG's are shown as examples in Table B. The variable sumwt is incremented by that DRG weight value, as indicated in step 99. After all the significant ICD codes have been processed for a given patient, the value of sumwt is the total of the weights assigned to the DRG's into which the codes are mapped.

Table B also contains, in column 4, a listing of the numbers of DRG's that are related to a given DRG in column 1, and which have Government assigned weights that are greater than that of the column 1 DRG, if any. The total number of such DRG's is given in column 3. The information of columns 3 and 4 of Table B are used in processing steps 101 and 103 to determine the magnitude of the variable sumdrg.

The concept of related DRG's, as embodied in column 4 of Table B, is explained in detail in U.S. Pat. No. 4,667,292 of Iameter Incorporated, the assignee of the present application. Briefly, a DRG is "related" to another DRG if it is a possible alternate choice for medical reimbursement purposes. That is, related DRG's are those that could, with some degree of probability, result from the same principal diagnosis or procedures performed as a "working" DRG. For each DRG given in column 1 of Table B, those DRG's related to it whose Government assigned weights are greater than that of the principal DRG are listed in column 4.

By the time processing step 101 is commenced, the subject ICD code has already been mapped into a given DRG. In the processing step 101, that DRG is found in column 1 of Table B and its related DRG numbers read from column 4 for that DRG. The weights of each of the related DRG's are then determined, one at a time, by locating each DRG in turn in column 1 of Table B and reading its Government assigned weight from column 2. As each of these weights is read from column 2, the variable sumdrg is incremented an amount equal to the read values, in step 103. Thus, for each diagnostic ICD code being so processed, the sum of all of its related DRG weights in excess of the weight of the DRG into which the subject ICD code is mapped, are added to the sumdrg variable.

A next step 105 calls for determining whether the selected ICD code being processed is on a "cc" list. This is determined by use of Table A where column 7 contains a "0" if the ICD code is not on that list, or a "1" if it is. Whether a given ICD code is on the cc list or not is provided by the Federal Medical Reimbursement System.

In the step 107, it is asked whether the selected ICD code is on that list. If it is not, the next three processing steps are skipped, the processing jumping to step 115. On the other hand, if a "1" is detected in column 7 of Table A for the selected ICD code, the variable ncc is incremented by 1, as indicated in step 109 of FIG. 6. The variable ncc, at the conclusion of processing for a given patient, contains a count of all of the diagnosis ICD codes inputted for that patient which are on the cc list.

The next steps 111 and 113 determines and adds weights that have been assigned to those ICD codes that are on the cc list. The weight assigned to any given ICD code is provided in column 8 of Table A and is a 1, 2 or 3 depending upon a perceived importance of the condition identified by the ICD code number to the severity of a patient's illness in the usual case. The weight that is assigned to each ICD code is the result of a professional judgment. It will be noted that column 8 of Table A contains an "x" for each ICD wherein the value of column 7 is "0"; that is, no weight is assigned to those ICD's that are not on the cc list. Being on the cc list itself indicates the importance of a given ICD to the severity of the illness, in a typical case.

Step 111 reads the weight value of column 8 of Table A for the ICD code being processed and, in step 113, that weight is added to the sumcc variable. At the end of examining all of the diagnostic ICD codes for a single patient, that variable contains the desired sum of the weights of all of the codes that are on the cc list.

A next step 115 is to inquire whether there are any other diagnostic ICD codes inputted for this patient which have not been analyzed according to the process of steps 83–113. If there are any others to be analyzed, the processing returns to step 83 and another diagnosis ICD code is taken through the same processing steps. When they have all been processed, five of the seven variables have been determined for that patient.

A sixth variable, namely mdcs, is determined in steps 117 and 119. Each of the intermediate variables $MDC_1$, $MDC_2$ ... $MDC_{23}$ into which any of the significant ICD codes were mapped by step 91 contain some non-zero value as the result of being incremented by 1 in step 93. In step 117 the number of such categories that are not 0 are tested. In step 119, the variable mdcs is then set equal to that count.

The six variables determined by this point of the processing have not utilized procedure ICD codes for their determination. The seventh variable does so and is determined by steps 121–127 of FIG. 6. In the step 121, a single procedure ICD code inputted for that patient is selected and, in step 123, compared with those listed on Table A to determine if it is a significant ICD. In step 125 it is determined whether the selected procedure ICD code is on the list of Table A and, if not, the next step 127 is omitted. If it is, however, the step 127 is implemented by incrementing the variable nproc by 1.

In a final step 129 of FIG. 6, it is asked whether there are any additional procedure ICD codes to be analyzed, and if so, the process returns to step 121 to begin that process for another procedure ICD code for the patient. If not, the nproc variable is at a value that is equal to the number of procedure ICD codes for the patient that are considered significant by inclusion in Table A. At the end of step 129, all seven variables have been calculated for a given patient.

The third major part of the processing involved in the example being described is shown in the flow chart of FIG. 7. A first step 31 in this part of the processing sets four result fields to 0: PLOS1, PLOS2, PLOS3 and PLOS. Each of the first three quantities is an intermediate result, the quantity PLOS being the result of the processing part shown in FIG. 7.

A next step 133 is to read the numerous multiplier constants from Tables C, D and E for the single DRG that has initially been determined for the patient. There are 24 such constants all together. An actual set of such constants is shown for a few DRG's in the attached Tables C, D and E.

The first intermediate quantity determined is PLOS1, the constants for doing so being given in Table C. All of the other constants of Tables C, D and E are used in the processing of FIG. 7 as multipliers of other information, except for the constant shown in the first column of Table C. In step 135, the constant read from that table directly increments the intermediate variable PLOS1.

In a step 137, the remaining 9 constants read from Table C for the given DRG are used as multipliers of patient specific information. As shown in step 137 of FIG. 7, the constant g11 is multiplied by the age of the patient. That result is then added to PLOS1. Next, the constant g12 is multiplied the numerical code for the patient's sex, and that result is added to PLOS1. The remaining seven constants g21 through g27 are individually multiplied times one of the variables calculated in previous processing described with respect to FIG. 6, and those results are individually added to the intermediate quantity PLOS1. The result is a single value PLOS1 that is used later in step 143.

Step 139 does a similar calculation involving seven terms, one for each of the seven variables determined by the processing of FIG. 6. Each of these terms, as clearly shown in step 139 of FIG. 7, contains one of the constants g31 through g37 from Table D. In addition, each of these quantities is multiplied by the patient's age. Each of these multiplications is accomplished, one at a time, and the result added to the variable PLOS2. The resulting value for PLOS2 is then held for use in step 143.

Similarly, in step 141, an intermediate variable PLOS3 is determined by multiplying each of the seven variables determined by the processing of FIG. 6 by one of the constants g38 through g3e of Table E, and the numerical code for the sex of the patient. A sum of those seven multiplications is added to the intermediate variable PLOS3.

In step 143, each of the intermediate variables PLOS1, PLOS2 and PLOS3 are added to become the resulting PLOS. This result is a prediction of the number of days a patient whose data is being analyzed should spend in the hospital for the indicated condition(s).

The constants of Tables C, D and E are determined from actual patient data in a manner described in the following section entitled "Determining Algorithm Constants". It will be noted from the examples of constants given in Tables D and E, which are used in the processing steps 139 and 141 of FIG. 7, that most of them are 0. This is the result of learning from the statistical analysis of actual data that many of the terms cross-multiplied by age and sex are not statistically significant. However, for those DRG's where one or more of the constants of Tables D and E is some non-zero value, it has been found to be significant in calculating the resultant length of stay prediction.

The result of the processing of FIG. 7 may optionally be classified into one of a few categories (acuity indices) for the DRG assigned to this patient, in a manner earlier described with respect to FIG. 2. A software algorithm is shown in FIG. 8 for taking the resultant length of stay prediction PLOS and determining which of five acuity index categories it belongs for the patient being analyzed.

A first step 145 is to read four constants from Table F. These constants show the breakpoints between the five index categories of predicted length of stay for each DRG. These constants g41 through g44 are determined by analyzing a large amount of actual patient data in a manner described in the following section entitled "Determining Algorithm Constants", an example of which is given in the computer programs attached hereto as Appendices A and B.

After those four constants have been acquired for the current calculation, the step 147 compares the PLOS with the constant g42. The constant g42 specifies the breakpoint between index categories 2 and 3. If PLOS is less than that value, a next step 149 asks whether the PLOS is equal to or less than g41, the breakpoint between the index categories 1 and 2. If so, the processing of FIG. 8 gives a result 151 that the PLOS quantity is within the index category 1. If not less than the constant g41, but since it is less than the constant g42, a result 153 is that the index category is 2.

However, if the response to the question of step 147 is that the PLOS is not equal or less than the constant g42, a next step 155 asks whether it is equal to or less than the constant, g43. The constant g43 is the breakpoint between index categories 3 and 4. If it is, then the result 157 must be that the index category is 3 for that PLOS. If not, a next step 159 asks whether PLOS is less than the constant g44, which is the breakpoint between index categories 4 and 5. If it is, the result 161 must be that the index category is 4. If not, the result is that the index category is 5.

Determining Algorithm Constants

The preceding example described with respect to the software flow diagrams of FIGS. 6–9 has available to it a large number of constants that are part of the static database, illustrated in Tables C–F. As discussed before, a separate set of such constants exists for each DRG. This section will outline a preferred technique for determining those constants for one DRG.

The constants are calculated by using a large amount of actual patient data. There are many available data bases that provide for each of millions of patients, his or her length of stay (LOS) in the hospital, age, sex, ICD diagnosis and procedure codes, the DRG into which that patient's hospital stay was classified, and other discharge data that is regularly maintained. With actual patient data, these variables of the previously discussed algorithm are known, and it is the constants that are to be determined, opposite to the situation when the system is used as described with respect to the example of FIGS. 6–8.

From the large number of patient records, a controlled number are randomly selected for each DRG. It has been found that 1,000 records per DRG is sufficient to give good results. A first step in the process of calculating the constants for a given DRG is to determine the value of the seven intermediate variables of the foregoing algorithm (ndx, sumwt, nmdcs, etc.) for each of the 1,000 patient records. The algorithm for doing this is preferably that described earlier with respect to FIG. 6. The result of determining these values, plus the information obtained from the patient records, allows the following equation to be set up, wherein each quantity is known except for the "constant" and the other constants g11, g12, g21 . . . which are to be determined:

$$LOS = \text{Constant} + (g11)(age) + (g12)(sex) +$$
$$(g21)(ndx) + (g22)(nproc) + (g23)(ncc) + (g24)(nmdcs) +$$
$$(g25)(sumwt) + (g26)(sumcc) + (g27)(sumdrg)$$

As a result of the information available, there will be 1,000 such equations which have the same 10 unknown quantities, namely the constants to be determined.

The next step is to determine optimal values for these constants for this one DRG. This is preferably accomplished by computer assisted regression analysis performed with an available statistical software package, such as that known as SAS. Such software chooses the unknown constants to minimize a sum of the squares of the differences between (1) all of the actual LOS's and (2) the predicted LOS's as calculated with the above equation for the sampled set of data and with a set of constants whose values are calculated with the statistical package.

After this is accomplished, each of the cross-product variable terms of steps 139 or 141 of FIG. 7 is added to the above equation one at a time, and the regression analysis is done once again. The reductions of error variance from the prior calculation that result from each added term are then measured. The term generating the largest reduction is then considered for inclusion in the model. If the amount of error variance reduction is not significant at the 0.01 level, then the constant for that term is set to zero, effectively discarding the term and all other cross-product terms which are not yet in the model. However, if the level of error variance by use of the term is greater than that threshold, this indicates that its use will result in a reduced variance between the actual LOS and predicted LOS, so it is retained.

After a first cross-product is retained, then the above-described process is repeated with all remaining cross-product terms, adding in the one that best reduces error variance. Once a term has been found useful and is retained in the equation, it is retained for all further stepwise calculations of additional terms. When the best term of a new calculation no longer meets the 0.01 level of significance, the process is stopped.

When this regression analysis has been made for the actual patient data for each of the DRG's of interest, then the constants previously described in the portion of the static data base of Tables C, D and E are all calculated. As a result, all of the constants necessary for operation of the algorithm of FIG. 7 are developed. This allows the calculation of an estimated LOS to be made. But as described before, it is generally desired to go further to express each patient's outcome in terms of one of the categories 1-5 of FIG. 2, using the algorithm of FIG. 8. The FIG. 8 algorithm requires four constants $g41-g44$ to exist in the computer static data base for each DRG, examples of which are given in Table F. That portion of the static data base may be developed by statistical techniques, part of which are illustrated in FIGS. 9-11.

FIG. 9 shows a distribution of about 1,000 points, one for each of the patient record samples selected for a single DRG, in this case DRG number 154. Consistent with the orientation of the curve of FIG. 2, the vertical axis for each sample point is its actual length of stay (LOS) and a horizontal axis is the predicted length of stay. The horizontal coordinate for each point is the LOS calculated by the algorithms of FIGS. 6 and 7. Each of the sampled patient records is expressed in FIG. 9 by a single point.

A first step in determining these four breakpoint constants for the example being described, is to reduce the large number of samples to a smaller number in a smoother pattern. The result of this step on the data illustrated in FIG. 9 is given in the fewer points, usually 20-40 for the data of each DRG, as illustrated in FIG. 11. The algorithm for smoothing and reducing the data in this way is illustrated with respect to FIG. 10. Each adjacent pair of data points of FIG. 9, such as points 201 and 203 of FIG. 10, are averaged into a single cluster 205, whenever the difference in the coordinates of the pair of points have different signs. That is, with respect to the example of FIG. 10, this condition is satisfied because the point 203 has a higher predicted LOS than the point 201 but a lower actual LOS. If the two coordinates of two adjacent data points both change in the same direction, no such average is taken.

Once the original data points are represented by a defined cluster, such as point 205, the original data points, such as 201 and 203, are discarded. The cluster 205 is then considered a data point that is again averaged with adjacent other raw data points or other clusters in the same way whenever the criteria of an inconsistent coordinate change illustrated in FIG. 10 is met. Such averaging is weighted by the number of points represented by a cluster. The averaging process is performed several times in succession, perhaps 8-10 times, until the only actual data points and clusters of data points remaining satisfy the criteria that the actual and predicted LOS of adjacent points/clusters changes in the same direction. That is the result illustrated in FIG. 11. In addition to smoothing the data and reducing the number of points to a more manageable number, this process reduces inconsistencies in the correspondence between the actual and predicted LOS's.

A special purpose computer program written in the Basic language is given in Appendix A hereto as an example of a specific implementation of the smoothing process described with respect to FIGS. 9-11. The data that is remembered for each averaged, cluster point of FIG. 11 is as follows: its average actual and average predicted LOS coordinates, the number of patient data points that have contributed to that averaged cluster point, the variance of actual LOS among the individual patient samples making up that average, and the largest and smallest predicted LOS of all the patient samples that make up the averaged cluster point.

The next step, not illustrated in the drawings, is to determine the four breakpoint constants for a given DRG from the description of the averaged cluster data points resulting from running the computer program of Appendix A hereto. This calculated data, plus the Government designated mean LOS for the DRG, is processed by a computer program of Appendix B hereto, which is also written in the Basic language. That software is designed to determine the breakpoints between the acuity index categories in order to minimize the variance between data points within each of the resulting five acuity index categories, while maximizing the variance between the average of each of these five categories. The example software of Appendix B does this by a trial and error method which calculates such variances for practically any possible set of four breakpoints and then selects the set that has this defined maximum and minimum. This example is also subject to the constraint that the Government designated mean LOS for the given DRG must lie within the middle acuity index category, between breakpoints $g42$ and $g43$ that are being calculated.

Once the points and clusters of points are so grouped into five categories, the actual breakpoints $g41$, $g42$, $g43$ and $g44$ are determined for one DRG by averaging the largest predicted LOS of individual patient samples represented by the highest cluster point of one category and the smallest predicted LOS contained in a cluster point in the next highest category.

General Discussion

The computer programs of Appendices A and B hereto contain material in which a claim of copyright is made by Iameter Incorporated, the assignee hereof. This assignee has no objection to the duplication of Appendices A and B hereto by photocopying and the like but reserves all other copyright therein.

The specific techniques described above have been directed to the prediction of likely resource consumption in terms of patient length of stay (LOS) or charges. However, resource consumption is only one of several possible outcomes of a patient stay in a hospital that may be measured by the present system as an indication of the quality of patient care. Others include patient mortality rate, morbidity rate, readmission rate, and rate of return to the operating room.

Although the various aspects of the present invention have been described with respect to a specific, preferred embodiment thereof that utilizes existing diagnoses and procedure classification systems adopted as part of a government mandated reimbursement system, it will be understood that the invention is entitled to protection within the full scope of the appended claims. It will be recognized that the techniques of the present invention have application to sub-categorizing any system of defining and expressing diagnoses, in order to explain resulting wide variations in the outcomes of treatment of a group of patients that all have the same diagnosis, by the use secondary diagnoses and other patient information.

TABLE I

SAMPLE DIAGNOSIS RELATED GROUPS (DRGs) AS PUBLISHED IN FEDERAL REGISTER SEPTEMBER 1, 1983

| DRG | MDC | SEX | TITLE | RELATIVE WEIGHT | MEAN LOS | OUTLIER CUTOFFS |
|---|---|---|---|---|---|---|
| 31 | 1 MED | B | CONCUSSION AGE >69 AND/OR C.C. | 0.6051 | 4.6 | 25 |
| 32 | 1 MED | B | CONCUSSION AGE 18-69 WITHOUT C.C. | 0.4519 | 3.3 | 19 |
| 33 | 1 MED | B | CONCUSSION AGE 0-17 | 0.2483 | 1.6 | 5 |
| 34 | 1 MED | B | OTHER DISORDERS OF NERVOUS SYSTEM AGE >69 AND/OR C.C. | 0.9927 | 7.1 | 27 |
| 35 | 1 MED | B | OTHER DISORDERS OF NERVOUS SYSTEM AGE <70 WITHOUT C.C. | 0.8480 | 6.2 | 26 |
| 96 | 4 MED | B | BRONCHITIS & ASTHMA AGE >69 AND/OR C.C. | 0.7996 | 6.9 | 24 |
| 97 | 4 MED | B | BRONCHITIS & ASTHMA AGE 18-69 WITHOUT C.C. | 0.7256 | 6.2 | 21 |
| 98 | 4 MED | B | BRONCHITIS & ASTHMA AGE 0-17 | 0.4275 | 3.7 | 11 |
| 261 | 9 SURG | F | BREAST PROC FOR NON-MALIG EXCEPT BIOPSY & LOC EXC | 0.7329 | 4.8 | 19 |

TABLE II

SAMPLE GROUPINGS OF ICD-9CM CODES INTO DRG CATEGORIES

DRG 31, CONCUSSION AGE = 70 AND/OR C.C. PRINCIPAL DIAGNOSIS

| Code | Description |
|---|---|
| 8500 | Concussion w/o Coma |
| 8501 | Concussion-Brief Coma |
| 8502 | Concussion-Moderate Coma |
| 8503 | Concussion-Prolong Coma |
| 8504 | Concussion-Deep Coma |
| 8505 | Concussion W Coma NOS |
| 8509 | Concussion NOS |

DRG 32, CONCUSSION AGE 18-69 WITHOUT C.C. PRINCIPAL DIAGNOSIS

| Code | Description |
|---|---|
| 8500 | Concussion w/o Coma |
| 8501 | Concussion-Brief Coma |
| 8502 | Concussion-Moderate Coma |
| 8503 | Concussion-Prolong Coma |
| 8504 | Concussion-Deep Coma |
| 8505 | Concussion W Coma NOS |
| 8509 | Concussion NOS |

DRG 33, CONCUSSION AGE 0-17 PRINCIPAL DIAGNOSIS

| Code | Description |
|---|---|
| 8500 | Concussion w/o Coma |
| 8501 | Concussion-Brief Coma |
| 8502 | Concussion-Moderate Coma |
| 8503 | Concussion-Prolong Coma |
| 8504 | Concussion-Deep Coma |
| 8505 | Concussion W Coma NOS |
| 8509 | Concussion NOS |

DRG 261, BREAST PROC FOR NON-MALIG EXCEPT BIOPSY & LOC EXC OPERATING ROOM PROCEDURES

| Code | Description |
|---|---|
| 8522 | Quadrant Resect Breast |
| 8523 | Subtotal Mastectomy |
| 8524 | Exc Ectopic Breast Tissu |
| 8525 | Excision of Nipple |
| 8531 | Unilat Reduct Mammoplast |
| 8532 | Bilat Reduct Mammoplasty |
| 8533 | Unil Subq Mammect-Implnt |
| 8534 | Unilat Subq Mammect NEC |
| 8535 | Bil Subq Mammect-Implant |
| 8536 | Bilat Subq Mammectom NEC |
| 8541 | Unilat Simple Mastectomy |
| 8542 | Bilat Simple Mastectomy |
| 8543 | Unilat Exten Simp Mastec |
| 8544 | Bilat Extend Simp Mastec |
| 8545 | Unilat Radical Mastectom |
| 8546 | Bilat Radical Mastectomy |
| 8547 | Unil Ext Rad Mastectomy |
| 8548 | Bil Exten Rad Mastectomy |
| 8550 | Augment Mammoplasty NOS |
| 8553 | Unilat Breast Implant |
| 8554 | Bilateral Breast Implant |
| 856 | Mastopexy |
| 857 | Total Breast Reconstruct |
| 8586 | Transposition of Nipple |
| 8587 | Nipple Repair NEC |
| 8589 | Mammoplasty NEC |
| 8593 | Breast Implant Revision |
| 8594 | Breast Implant Removal |
| 8599 | Breast Operation NEC |

TABLE A

| (1) ICD Codes | (2) Male <70 | (3) Male ≧70 | (4) Fem. <70 | (5) Fem. ≦70 | (6) MDC | (7) CCOR | (8) CCWGT |
|---|---|---|---|---|---|---|---|
| D0040 | 183 | 182 | 183 | 182 | 6 | 0 | X |
| D1277 | 183 | 182 | 183 | 182 | 6 | 0 | X |
| D39891 | 127 | 127 | 127 | 127 | 6 | 1 | 2 |
| D4111 | 140 | 140 | 140 | 140 | 5 | 1 | 2 |
| D4800 | 90 | 89 | 90 | 89 | 4 | 0 | X |
| D485 | 90 | 89 | 90 | 89 | 4 | 1 | 2 |

(columns 2-5 headed: MAPPED INTO DRG'S)

TABLE B

| DRG's | Weight | nworse | Related DRG's |
|---|---|---|---|
| 89 | 1.1657 | 3 | 79, 80, 423 |
| 90 | 0.8842 | 8 | 79, 80, 85, 86, 88, 89, 92, 423 |
| 127 | 1.0098 | 3 | 121, 124, 129 |
| 140 | 0.6894 | 6 | 121, 122, 124, 125, |

TABLE B-continued

| DRG's | Weight | nworse | Related DRG's |
|---|---|---|---|
| 182 | 0.6032 | 7 | 132, 133<br>174, 175, 176, 177,<br>179, 180, 188 |
| 183 | 0.5104 | 11 | 174, 175, 176, 177,<br>178, 179, 180, 181<br>182, 188, 189 |

TABLE C

| DRG's | Constant | g11 | g12 | g21 | g22 | g23 | g24 | g25 | g26 | g27 |
|---|---|---|---|---|---|---|---|---|---|---|
| 89 | 1.5603 | 0.0625 | −1.5942 | −1.4643 | 0.0000 | 1.7509 | 0.0225 | 1.7797 | 0.3199 | −0.0705 |
| 90 | 0.7835 | 0.0034 | −0.1413 | 0.0856 | 0.0000 | 0.3699 | −0.1795 | 0.0167 | 0.0000 | −0.0037 |
| 127 | 3.6392 | 0.0136 | −1.0203 | −2.6294 | 0.0000 | 0.4099 | 0.5988 | 2.8201 | −0.5819 | 0.0642 |
| 140 | 0.5561 | 0.0053 | 0.0248 | −0.1671 | 0.0000 | 0.0617 | 0.0633 | 0.1597 | −0.0189 | 0.0091 |
| 812 | −0.0963 | 0.0131 | 0.1415 | 0.0537 | 0.0000 | −0.0748 | −0.0147 | 0.0969 | 0.0567 | 0.0060 |
| 183 | 0.2914 | 0.0063 | 0.1628 | 0.2601 | 0.0000 | −0.0526 | −0.0552 | −0.0023 | 0.0000 | −0.0150 |

TABLE D

| DRG's | g31 | g32 | g33 | g34 | g35 | g36 | g37 |
|---|---|---|---|---|---|---|---|
| 89 | 0.0000 | 0.0000 | 0.0000 | 0.0000 | 0.0000 | −0.0133 | 0.0000 |
| 90 | 0.0000 | 0.0000 | 0.0000 | 0.0000 | 0.0000 | 0.0000 | 0.0000 |
| 127 | 0.0000 | 0.0000 | 0.0000 | 0.0000 | 0.0000 | 0.0000 | 0.0000 |
| 140 | 0.0000 | 0.0000 | 0.0000 | 0.0000 | 0.0000 | 0.0000 | 0.0000 |
| 182 | 0.0000 | 0.0000 | 0.0000 | 0.0000 | 0.0000 | 0.0000 | −0.0002 |
| 183 | 0.0000 | 0.0000 | 0.0000 | 0.0000 | 0.0000 | 0.0000 | 0.0000 |

TABLE E

| DRG's | g38 | g39 | g3a | g3b | g3c | g3d | g3e |
|---|---|---|---|---|---|---|---|
| 89 | 0.5128 | 0.0000 | 0.0000 | 0.0000 | 0.0000 | 0.0000 | 0.0000 |
| 90 | 0.0000 | 0.0000 | 0.0000 | 0.0187 | 0.0000 | 0.0000 | 0.0000 |
| 127 | 0.0000 | 0.0000 | 0.0000 | 0.0000 | 0.0000 | 0.3213 | 0.0000 |
| 140 | 0.0000 | 0.0000 | 0.0000 | 0.0000 | 0.0000 | 0.0000 | 0.0000 |
| 182 | 0.0000 | 0.0000 | 0.0000 | 0.0000 | 0.0000 | 0.0000 | 0.0000 |
| 183 | 0.0000 | 0.0000 | 0.0000 | 0.0000 | 0.0000 | 0.0000 | 0.0000 |

TABLE F

| DRG's | g41 | g42 | g43 | g44 |
|---|---|---|---|---|
| 89 | 5.486 | 8.099 | 12.467 | 13.896 |
| 90 | 1.234 | 1.445 | 1.584 | 1.996 |
| 127 | 7.214 | 9.253 | 10.226 | 13.772 |
| 140 | 1.046 | 1.138 | 1.405 | 1.491 |
| 182 | 0.839 | 1.135 | 1.487 | 1.614 |
| 183 | 0.652 | 0.949 | 1.387 | 1.555 |

APPENDIX A

Data Smoothing Program (©, Iameter 1986)

```
'Program to smooth predicted and actual LOS's
'
'The DRG for which data are to be smoothed is input on the command line.
'The program then opens the file "DRGxxx.DAT" (where xxx is the DRG number)
'for input and "SMTHxxx.DAT" for output.  The input file has been sorted in
'increasing order of predicted LOS.  Each record has predicted LOS in
'columns 4-8 and actual LOS in columns 12-19.  The output file has four
'fields per record: actual LOS, predicted LOS, smoothed predicted LOS and
'smoothed actual LOS.  Each field takes 8 columns and is written with 3
'decimals.
'
'The actual and predicted LOS's are stored in LOS() and PLOS().  Their
'smoothed counterparts are XNEW() and YNEW().  The previous interation uses
'XOLD() and YOLD() to hold these values.
```

```
dim los(1300),plos(1300),xnew(1300),ynew(1300),xold(1300),yold(1300)
j = 0                                       'j indexes input records
key off
key (1) on
on key (1) gosub abort                      'set up panic button
locate 1,1,1
drg$ = command$                             'get DRG number
f1$ = "DRG" + drg$ + ".DAT"                 'input file
f2$ = "SMTH" + drg$ + ".DAT"                'output file
open f1$ for input as #1
locate 25,1
print "Now reading:";
while(not(eof(1)))                          'input loop
    j = j + 1                               'increment record counter
    locate 25,14,0
    print j;
    line input#1,nn$
    los(j) = val(mid$(nn$,4,8))             'actual LOS
    plos(j) = val(mid$(nn$,12,8))           'predicted LOS
    xold(j) = plos(j)                       'initialize values from previous
    yold(j) = los(j)                        'iteration
wend
close#1
pass = 0                                    'counts number of smoothing passes
nobs = j                                    'total number of observations smoothit:
pass = pass + 1
locate 25,1                                 'display pass counter
print "Pass:" + spc$(20);
locate 25,40
print "N:";
locate 25,7,0
print pass;
n = 0                                       'n counts input records
nout = 0                                    'nout counts smoothed records
getnext:
n = n + 1
locate 25,43,0                              'show action indicator
print n;
if n = 1 then gosub initial                 'initialize if 1st observation
if yold(n) > yy and nn <> 0 then
    gosub unique                            'stop the averaging
    gosub initial
end if
yy = (nn * yy + yold(n)) / (nn + 1)         'average in yold(n) with yy
xx = (nn * xx + xold(n)) / (nn + 1)         'average in xold(n) with xx
nn = nn + 1                                 'nn counts obs being averaged
if n = nobs then gosub unique else goto getnext 'if last obs then done
for j = 1 to nobs - 1                       'check to see if another pass is
    if ynew(j) > ynew(j + 1) then           'needed, if so goto onemore
        gosub onemore
        goto smoothit
    end if
next
open f2$ for output as #2                   'no more needed, write output file
locate 25,1
print"Now writing:" + spc$(20);
for j = 1 to nout
    locate 25,14,0
    print j;
    print#2,using"####.###";los(j);plos(j);xnew(j);ynew(j)
next
close
locate 20,1
print pass;"passes required";
system
```

```
onemore:
for j = 1 to nobs                              'put new array into old
    xold(j) = xnew(j)
    yold(j) = ynew(j)
next
return initial:                                       'initialize x,y totals being average
xx = 0
yy = 0
nn = 0
return unique:                                        'the xx and yy values constitute a
for k = 1 to nn                                'unique plos & los
    xnew(nout + k) = xx
    ynew(nout + k) = yy
next
nout = nout + nn
return abort:
system
```

APPENDIX B

Break Point Determining Program (©, Iameter 1986)

```
'Program to search all possible partitions for the one which maximizes RIV
'(reduction in variance) between the total LOS variance in a DRG and the
'sum of the within AIM category variances. The input file to this program
'is the output file from EXPORT. See step 6 of model outline.
'
'    Input arrays
'        mnprdlos     mean predicted LOS for each LOS group
'        meanlos      mean actual LOS for each LOS group
'        npts         number of patients in each LOS group
'        varlos       variance of actual LOS within LOS group
'
'    Output arrays
'        ppl          pooled predicted LOS for each AIM group
'        pml          pooled mean LOS for each AIM group
'        pn           pooled number of patients for each AIM group
'        pvar         pooled within AIM group variance of LOS
'
'    Other arrays
'        cp           holds the four cut-points which define the input records
'                     which are being pooled. For example, if cp(1)=1, cp(2)=
'                     3, cp(3)=5, and cp(4)=8 then AIM category 1 would consist
'                     of input record 1 only, AIM 2 would include records 2 and
'                     3, AIM 3 would include 4 and 5, AIM 4 would include
'                     records 6 through 8 and AIM 5 would have the rest.
'        cpsave       holds the cut-points which resulted in the maximum R2 up
'                     to that time.
dim mnprdlos(50),meanlos(50),npts(50),varlos(50)
dim ppl(5),pml(5),pn(5),pvar(5)
dim cp(4),cpsave(4)
input"Enter the DRG number: ",drg$
drg = val(drg$)
input"Enter the total variance of LOS for this DRG: ",totvar
input"Is regression done on log LOS? ",a$
nchk = 0
if a$="Y" or a$="y" then
    loglos=1
    w$ = "geometric"
else
    loglos=0
    w$ = "arithmetic"
end if
```

```
print"Enter the government ";w$;" mean LOS for this DRG: ";:input"",amean
if loglos=1 then amean=log(amean)
NAIMCAT = 5                                    'define number of AIM categories
NAIMM1 = NAIMCAT - 1                           'define # AIM categories minus 1
f1$ = "sum" + drg$ + ".dat"                    'define input, output files
f2$ = "res" + drg$ + ".dat"
key off:key (1) on:on key(1) gosub abort       'turn on panic button
open f1$ for input as #1                       'open input, output files
open f2$ for output as #2
ncat = 0                                       'count number of LOS categories
while (not eof(1))                             'loop over input records
    line input#1,temp$
    ncat = ncat + 1
    mnprdlos(ncat) = val(mid$(temp$,1,10))     'mean pred. LOS in cols 1-10
    meanlos(ncat) = val(mid$(temp$,11,10))     'mean LOS in cols 11-20
    npts(ncat) = val(mid$(temp$,21,10))        'n of pts in cols 21-30
    varlos(ncat) = val(mid$(temp$,31,15))      'LOS variance in cols 31-45
wend
rivmax = 0                                     'initialize max riv
for j = 1 to NAIMM1                            'initialize cut-points
    cp(j) = j
next j nextiter:
nchk = nchk + 1
locate 25,1                                    'display current cut-points
for j = 1 to NAIMM1
    print cp(j);
next j
gosub pool                                     'pool categories as defined in cp
gosub rivcalc                                  'calculate riv value
if riv > rivmax then
    rivmax = riv                               'update rivmax and cpsave
    for j = 1 to NAIMM1
        cpsave(j) = cp(j)
    next j
end if k = NAIMM1                                     'increment cut-points
while (k > 0)
    while (cp(k) < (ncat + k - NAIMCAT))
        cp(k) = cp(k) + 1
        if k < NAIMM1 then
            for j = k + 1 to NAIMM1
                cp(j) = cp(j - 1) + 1
            next j
        end if
        goto nextiter
    wend
    k = k - 1
wend
for j = 1 to NAIMM1                            'if k = 0 then we are done
    cp(j) = cpsave(j)                          'put best cut-points back in and
next j                                         'recreate best pooling
locate 15,1
print nchk;" collapsings checked";
gosub pool
gosub rsquare                                  'also calculate rsquare
for aim = 1 to NAIMCAT                         'output results
    print#2,using"###";drg;
    print#2,using"#########.##";ppl(aim);pml(aim);
    print#2,using"######";pn(aim);
    print#2,using"##########.#####";pvar(aim);
    if aim = NAIMCAT then
        print#2,
        print#2,using"###";drg;                'write summary record
        print#2,using"####.###";rivmax;        'write max reduct. in var.
        print#2,using"###.####";r2;            'rsquare and the optimal cut-points
```

```
        for k = 1 to NAIMM1
            print#2,using"###";cpsave(k);
        next k
        for k = 1 to NAIMM1
            cp = (mnprdlos(cpsave(k)) * npts(cpsave(k)) +_
                  mnprdlos(cpsave(k) + 1) * npts(cpsave(k) + 1)) /_
                  (npts(cpsave(k)) + npts(cpsave(k) + 1))
            print#2,using"####.###";cp;
        next
        print#2,
    else
        print#2,
    end if next aim
system pool:
for aim = 1 to NAIMCAT                        'pool categories as defined by
    n = 0                                     'cp values
    sumprd = 0
    sumlos = 0
    totwith = 0
    if aim = 1 then first = 1_                'define 1st record for AIM group
        else first = last + 1
    if aim = NAIMCAT then last = ncat_        'define last record
        else last = cp(aim)
    for irec = first to last                  'pool n, predicted LOS, actual
        n = n + npts(irec)                    'LOS and within variance
        sumprd = sumprd + npts(irec) * mnprdlos(irec)
        sumlos = sumlos + npts(irec) * meanlos(irec)
        totwith = totwith + (npts(irec) - 1) * varlos(irec)
    next irec
    ppl(aim) = sumprd / n                     'save results for AIM category
    pml(aim) = sumlos / n
    pn(aim) = n
    ssb = 0                                   'compute sum of squares between
    for irec = first to last                  'categories being pooled to add to
        ssb = ssb + npts(irec) * (meanlos(irec) - pml(aim))^2
    next irec                                 'total within variance
    pvar(aim) = 0:if n > 1 then pvar(aim) = (ssb + totwith) / (n - 1)
next aim
return rivcalc:
if pml(3) < .8 * amean or_                    'routine to calculate RIV
   pml(3) >1.2 * amean then                   'reject if AIM category 3 mean
    riv = -1                                  'is more than 20% from actual mea
    return
end if
withvar = 0
for aim = 1 to NAIMCAT
    withvar = withvar + (pn(aim) - 1) * pvar(aim)
next aim
riv = 100*((totvar - withvar) / totvar)
for aim = 1 to NAIMCAT
    if pn(aim) < 5 then riv = -1:return       'if any AIM category has less
next aim                                      'than 5 pts then don't use it
return rsquare:
sumx = 0
sumy = 0                                      'routine to compute rsquare
sumx2 = 0                                     'between AIM values 1 to 5 and
sumy2 = 0                                     'the mean LOS for the category
sumxy = 0
sumn = 0
for aim = 1 to NAIMCAT
```

```
    sumx = sumx + pn(aim) * aim
    sumy = sumy + pn(aim) * pml(aim)
    sumn = sumn + pn(aim)
next aim
sumx = sumx / sumn
sumy = sumy / sumn
for aim = 1 to NAIMCAT
    sumxy = sumxy + pn(aim) * (aim - sumx) * (pml(aim) - sumy)
    sumx2 = sumx2 + pn(aim) * (aim - sumx)^2
    sumy2 = sumy2 + pn(aim) * (pml(aim) - sumy)^2
next aim
if sumx2 = 0 or sumy2 = 0 then return
r2 = sumxy^2 / (sumx2 * sumy2)
return abort:SYSTEM
```

It is claimed:

1. A method of monitoring the performance of a health provider in rendering medical services to a patient, comprising the steps of:
   (1) predicting an outcome of treatment of the patient by the health provider by a method including the following steps executed on a computer:
       converting into digital electronic signals input medical codes of at least a patient's principal diagnosis, any secondary diagnoses, any surgical procedures, sex and age,
       identifying a few of an existing plurality of diagnostic and/or procedure groups of illnesses that are appropriate for either one of the surgical procedures signals or the principal diagnosis signals,
       selecting from those few identified groups a single diagnostic or procedure group that is consistent with the signals of any secondary diagnoses and the patient's age and sex, and
       calculating a sub-category within the single selected diagnostic or procedure group for predicting at least one outcome by a formula that mathematically combines various of the medical code input signals with constants unique to the single selected diagnostic or procedure group, the constants having been determined from a statistical analysis of a large amount of actual patient data within the single selected diagnostic or procedure group by use of the same formula;
   (2) predicting from the calculated sub-category at least one outcome of patient treatment;
   (3) comparing said predicted outcome with the actual outcome of patient treatment;
   (4) monitoring the performance of health providers through use of said comparison; and
   (5) providing counseling to said health provider if the performance level of the health provider falls below an established level.

2. A method of monitoring the performance of a health provider in rendering medical services to a patient, comprising the steps of:
   (1) in a computer system having data of a medical patient that includes the patient's age, a numerical representation of the patient's sex, an ICD code of a principal diagnosis of the patient's condition, one or more ICD codes of secondary diagnosis of the patient's condition, and a DRG determined from the ICD codes in accordance with a Government grouper algorithm, a method of predicting by computer processing an outcome of treatment of the patient, comprising the steps of:
       providing a computer static data base that includes a first table of DRG categories into which each of a plurality of ICD codes is mapped, and a second table of Government mandated weights of the individual DRG categories,
       determining from the first table the DRG categories into which each of the ICD codes is mapped,
       reading from the second table the weights of each of the determined DRG categories,
       summing the read DRG weights, and
       predicting an outcome of the patient treatment by use of the sum of the read DRG weights;
   (2) comparing said predicted outcome with the actual outcome of patient treatment;
   (3) monitoring the performance of health providers through use of said comparison; and
   (4) providing counseling to said health provider if the performance level of the health provider falls below an established level.

3. A method according to claim 2 wherein the outcome predicting step includes estimating the length of hospital stay for the patient and classifying that stay length into one of a few categories within the DRG determined for the patent.

4. A method according to claim 2 wherein the method of predicting an outcome of treatment additionally comprises a step of counting the number of patient ICD diagnosis codes, and wherein the outcome calculation step includes use of said ICD code count in estimating the outcome.

5. A method according to claim 4 wherein, in the method of predicting an outcome of treatment, the computer system additionally includes one or more ICD codes of the procedures performed or to be performed on the patient, and wherein the outcome predicting method additionally comprises a step of counting the number of patient ICD procedure codes, and further wherein the outcome calculation step includes use of said ICD code count in predicting the outcome.

6. A method according to claim 5 wherein, in the method of predicting an outcome of treatment, the first table of the static data base also includes a MDC body system category into which each ICD code is mapped, and wherein the outcome estimating method additionally comprises a step of counting the number of MDC categories in which the patient ICD codes map, and further wherein the outcome calculation step includes the use of said MDC category count in predicting the outcome.

7. A method according to claim 2 wherein, in the method of predicting the outcome of treatment,
the first table of the static data base also includes an indication for the individual ICD codes whether each is on a Government list of ICD codes that can indicate the existence of a complication or co-morbidity, and, if so, also indicates a weight of severity of the condition indicated by each such ICD code,
said method additionally comprising the steps of reading the weight of the patient's ICD codes and summing those weights, and
further wherein the outcome calculation step includes the use of the sum of said weights in estimating the outcome.

8. A method according to claim 2 wherein, in the method of predicting the outcome of treatment,
the second table of the static data base also includes for individual DRGs one or more DRGs that are medically related thereto and which have higher Government assigned weights,
said method additionally comprising the steps of reading from the second table the related DRGs for each DRG into which a patient ICD code is mapped, and looking up in the first table the Government assigned weights for each of the related DRGs so read, and summing those read weights, and
further wherein the outcome prediction step includes the use of related DRG weight sum in predicting the outcome.

9. A method of monitoring the performance of a health provider in rendering medical services to a patient, comprising the steps of:
(1) for use with a system that estimates the amount of resources that are likely to be consumed to treat a specific patient illness by classifying the patient into one of a large number of categories of estimated resource consumption on the basis of input information that includes a principal diagnosis and/or a surgical procedure performed or to be performed, any secondary diagnoses, the patient's age and sex, a method of more accurately estimating an outcome of treatment of the patient by a health provider within said one category, comprising the following steps executed on a computer:
determining a category for each of a plurality of diagnoses and/or procedures of the input information as if it was the only diagnosis or procedure to be considered, and noting the resource estimate for each such category,
determining from said input information a plurality of other quantities relating to the patient's condition, and
calculating a refined resource estimate within the determined one category by solving an algebraic equation that combines the noted category resource estimates and the other quantities derived from the input information after multiplication by a plurality of constants, said constants having been derived by statistical analysis of a large amount of actual data of input information and the resources consumed by patients classified in said one category by use of said algebraic equation;

(2) comparing said calculated resource estimate with the amount of resources actually used;
(3) monitoring the performance of health providers through use of said comparison; and
(4) providing counseling to said health provider if the performance level of the health provider falls below an established level.

10. The method according to claim 9 wherein the step of determining a category includes doing so for each of the diagnoses in said input information but not for any surgical procedures therein.

11. The method according to claim 9 wherein the step of determining a category includes doing so for each of the principal and secondary diagnoses and surgical procedures in said input information.

12. The method according to claim 9 wherein the step of determining other quantities includes calculating by said computer the following from the input information:
a total of the number of different diagnoses,
a total number of any surgical procedures performed or to be performed, and
a number of different body systems involved as a result of the patient's illness.

13. A method of monitoring the performance of a health provider in rendering medical services to a patient, comprising the steps of:
(1) for use with a system that estimates the amount of resources that are likely to be consumed to treat a specific patient illness by classifying the patient into one of a large number of categories of estimated resource consumption on the basis of input information that includes a principal diagnosis and/or a surgical procedure performed or to be performed, any secondary diagnoses, the patient's age and sex, a method of forecasting an outcome of treatment of the patient by a health provider, comprising the following steps executed on a computer:
determining a plurality of quantities relating to the patient's illness, such a determination being made only from (A) the input information about the patient and the patient's illness that is used to determine said one category, and (B) a static database including but not limited to information about the categories, diagnoses, procedures and category estimated resource consumption, and
calculating a refined resource estimate within the determined one category by solving an algebraic equation that combines said plurality of quantities after multiplication by a plurality of constants, said constants having been derived from use of said algebraic equation by statistical analysis of a large amount of actual data of input information and the resources consumed by patients classified in said one category;
(2) comparing said calculated resource estimate with the amount of resources actually used;
(3) monitoring the performance of health providers through use of said comparison; and
(4) providing counseling to said health provider if the performance level of the health provider falls below an established level.

14. The method according to any of claims 9-13, inclusive, wherein said diagnoses and surgical procedures are expressed as ICD codes, said categories are diagnostic related groups (DRGs) of a health care reimbursement system, and the category resource estimates are Government designated weights of the individual DRGs.

15. A method of monitoring the performance of a health provider in rendering medical services to a given patient from patient information including illness diagnoses, surgical procedures performed or to be performed, if any, age and sex, comprising the steps of:

establishing on a computer a mathematical relationship of said treatment outcome with a plurality of variables developed from said patient information, inputing to the computer data including said information and resulting treatment outcomes for a large population of actual patients, utilizing the mathematical relationship to determine by calculations with the computer a set of elements in the mathematical relationship from said actual patient data which minimize differences between the actual outcomes and those calculated by said mathematical relationship from the actual patient information, forming by calculation on the computer the mathematical relationship variables from said given patient information, solving on the computer said mathematical relationship with said given patient variables and said determined set of elements, thereby to provide a prediction of the outcome of treatment for said given patient;

comparing said predicted outcome with the actual outcome of patient treatment;

monitoring the performance of health providers through use of said comparison; and providing counseling to said health provider if the performance level of the health provider falls below an established level.

16. A method according to claim 15 wherein the outcome of treatment includes the level of resources expended in providing patient treatment.

17. A method according to claim 15 wherein the step of forming the variables includes the steps of forming from said patient information at least a first variable that is proportional to the total number of said diagnoses, and a second variable that is proportional to the total number of said surgical procedures performed or to be performed.

18. A method according to claim 15 wherein the step of forming the variables includes the step of forming a variable that is proportional to a sum of relative weights of groups of the diagnoses and/or procedures.

19. A method according to claim 15 wherein the step of establishing a mathematical relationship includes the steps of establishing a plurality of constants as said elements, and obtaining mathematical products of one or more of said variables by one of said constants, and then summing the products in order to obtain the outcome.

20. A method according to any one of claims 15-19 wherein the step of forming the mathematical relationship variables includes doing so only from patient information of illness diagnoses, surgical procedures performed or to be performed, if any, age and sex.

21. A method of monitoring the performance of a health provider in rendering medical services to a patient from patient information including illness diagnoses, surgical procedures performed or to be performed, if any, age and sex, comprising the steps of:

(1) in a computer system that includes means for mapping a medical patient's condition and/or treatment into a single group of related diagnoses and/or procedures from information of the patient that includes a principal diagnosis code, one or more surgical procedure codes, if any, one or more secondary diagnosis codes, if any, the patient's age, and the patient's sex, a method of predicting an outcome of treatment of the patient by a health provider by use of said computer system, comprising the steps of;

calculating a plurality of variables from said patient information, and mathematically combining said variables with the use of a plurality of constants that have been determined by statistical analysis of data from an actual patient population within said single group of related diagnoses and/or procedures, thereby to predict an outcome of treatment of the patient;

(2) comparing said predicted outcome with the actual outcome of patient treatment;

(3) monitoring the performance of health providers through use of said comparison; and (4) providing counseling to said health provider if the performance level of the health provider falls below an established level.

22. A method according to claim 21 wherein the outcome of treatment includes an indication of the level of resources expended in providing patient treatment.

23. A method according to claim 21 wherein the step of calculating a plurality of variables includes the steps of forming from said patient information at least a first variable that is proportional to the total number of said diagnoses, and a second variable that is proportional to the total number of said surgical procedures performed or to be performed, if any.

24. A method according to claim 21 wherein the step of calculating a plurality of variables includes the step of forming a variable that is proportional to a sum of relative weights of various groups of related diagnoses and/or procedures into which the diagnoses and/or procedures individually map.

25. A method according to claim 21 wherein the step of mathematically combining the variables includes obtaining a plurality of mathematical products of one or more of said variables by one of said constants, and then summing the products in order to obtain the outcome.

26. A method according to claim 21 wherein the steps of predicting of the outcome of treatment comprise the additional step of classifying the predicted outcome within one of a plurality of sub-categories within the determined single group of related diagnoses and/or procedures.

27. A method according to any one of claims 21-26 wherein the step of forming the mathematical relationship variables includes doing so only from patient information of illness diagnoses, surgical procedures performed or to be performed, if any, age and sex.

* * * * *

UNITED STATES PATENT AND TRADEMARK OFFICE
CERTIFICATE OF CORRECTION

PATENT NO.   :   5,018,067
DATED        :   May 21, 1991
INVENTOR(S)  :   William C. Mohlenbrock, et al.

It is certified that error appears in the above-identified patent and that said Letters Patent is hereby corrected as shown below:

Column 34, line 45, in Claim 3:     replace "patent" with --patient--

Column 34, line 50, in Claim 4:     replace "estimating" with --predicting--

Column 36, line 37, in Claim 13:    replace "a" with --the--

Column 37, line 10, in Claim 15:    replace "inputing" with --inputting--

Column 38, line 13, in Claim 21:    replace ";" with --:--

Signed and Sealed this

Twenty-second Day of December, 1992

Attest:

DOUGLAS B. COMER

*Attesting Officer*       Acting Commissioner of Patents and Trademarks